United States Patent
Herr et al.

(10) Patent No.: US 10,406,002 B2
(45) Date of Patent: Sep. 10, 2019

(54) CONTROLLING TORQUE IN A PROSTHESIS OR ORTHOSIS BASED ON A DEFLECTION OF SERIES ELASTIC ELEMENT

(71) Applicant: Bionx Medical Technologies, Inc., Bedford, MA (US)

(72) Inventors: Hugh Miller Herr, Somerville, MA (US); Richard J. Casler, Jr., Lowell, MA (US); Zhixiu Han, Acton, MA (US); Christopher Eric Barnhart, Carlisle, MA (US); Gary Girzon, Sudbury, MA (US); David Adams Garlow, Sanbornville, NH (US)

(73) Assignee: Bionx Medical Technologies, Inc., Bedford, MA (US)

( * ) Notice: Subject to any disclaimer, the term of this patent is extended or adjusted under 35 U.S.C. 154(b) by 788 days.

(21) Appl. No.: 14/150,840

(22) Filed: Jan. 9, 2014

(65) Prior Publication Data

US 2014/0121782 A1    May 1, 2014

Related U.S. Application Data

(63) Continuation of application No. 13/079,571, filed on Apr. 4, 2011, now abandoned.

(Continued)

(51) Int. Cl.
*A61F 2/68* (2006.01)
*A61F 2/70* (2006.01)
(Continued)

(52) U.S. Cl.
CPC .............. *A61F 2/70* (2013.01); *A61F 2/6607* (2013.01); *A61F 2/68* (2013.01); *A61F 5/0127* (2013.01);
(Continued)

(58) Field of Classification Search
CPC .................................. A61F 2/68; A61F 2/6607
See application file for complete search history.

(56) References Cited

U.S. PATENT DOCUMENTS

| 45,169 A | 11/1864 | Neubert |
| 360,446 A | 4/1887 | Kreemer |

(Continued)

FOREIGN PATENT DOCUMENTS

| EP | 1 393 866 A1 | 3/2004 |
| EP | 1 408 892 | 4/2004 |

(Continued)

OTHER PUBLICATIONS

Abbas J. and Chizeck H., Neural Network Control of Functional Neuromuscular Stimulation Systems: Computer Simulation Studies, IEEE Transactions on Biomedical Engineering, vol. 42, No. 1, Nov. 1995, pp. 1117-1127.

(Continued)

*Primary Examiner* — Bruce E Snow

(57) ABSTRACT

In some embodiments of a prosthetic or orthotic ankle/foot, a prediction is made of what the walking speed will be during an upcoming step. When the predicted walking speed is slow, the characteristics of the apparatus are then modified so that less net-work that is performed during that step (as compared to when the predicted walking speed is fast). This may be implemented using one sensor from which the walking speed can be predicted, and a second sensor from which ankle torque can be determined. A controller receives inputs from those sensors, and controls a motor's torque so that the torque for slow walking speeds is lower than the torque for fast walking speeds. This reduces the work performed by the actuator over a gait cycle and the peak actuator power delivered during the gait cycle. In some embodiments, a series elastic element is connected in series with a motor that can drive the ankle, and at least one sensor (Continued)

is provided with an output from which a deflection of the series elastic element can be determined. A controller determines a desired torque based on the output, and controls the motor's torque based on the determined desired torque.

7 Claims, 13 Drawing Sheets

Related U.S. Application Data

(60) Provisional application No. 61/432,083, filed on Jan. 12, 2011, provisional application No. 61/422,873, filed on Dec. 14, 2010, provisional application No. 61/320,991, filed on Apr. 5, 2010.

(51) Int. Cl.
| | |
|---|---|
| A61F 2/66 | (2006.01) |
| A61F 5/01 | (2006.01) |
| A61F 2/50 | (2006.01) |
| A61F 2/76 | (2006.01) |
| A61F 2/60 | (2006.01) |
| A61F 2/74 | (2006.01) |

(52) U.S. Cl.
CPC . *A61F 2002/5003* (2013.01); *A61F 2002/503* (2013.01); *A61F 2002/5007* (2013.01); *A61F 2002/5018* (2013.01); *A61F 2002/5033* (2013.01); *A61F 2002/607* (2013.01); *A61F 2002/6685* (2013.01); *A61F 2002/701* (2013.01); *A61F 2002/704* (2013.01); *A61F 2002/745* (2013.01); *A61F 2002/7625* (2013.01); *A61F 2002/7635* (2013.01); *A61F 2002/7645* (2013.01); *A61F 2002/7695* (2013.01); *A61F 2005/0155* (2013.01)

(56) References Cited

U.S. PATENT DOCUMENTS

| | | |
|---|---|---|
| 595,634 A | 12/1897 | King |
| 2,489,291 A | 11/1949 | Henschke et al. |
| 2,529,968 A | 11/1950 | Sartin |
| 3,098,645 A | 7/1963 | Owens |
| 3,207,497 A | 9/1965 | Schoonover |
| 3,546,712 A | 12/1970 | Tarte |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,697,808 A | 10/1987 | Larson et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,282,460 A | 2/1994 | Boldt |
| 5,294,873 A | 3/1994 | Seraji |
| 5,311,109 A | 5/1994 | Ozawa |
| RE34,661 E | 7/1994 | Grim |
| 5,327,790 A | 7/1994 | Levin et al. |
| 5,330,417 A | 7/1994 | Petersen et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,888,213 A | 3/1999 | Sears et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,095,991 A | 8/2000 | Krausman et al. |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,500,138 B1 | 12/2002 | Irby et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,532,400 B1 | 3/2003 | Jacobs |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,645,252 B2 | 11/2003 | Asai et al. |
| 6,660,042 B1 | 12/2003 | Curcie et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| 6,821,233 B1 | 11/2004 | Colombo et al. |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |

(56) References Cited

U.S. PATENT DOCUMENTS

| | | |
|---|---|---|
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,190,141 B1 | 3/2007 | Ashrafiuon et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,278,954 B2 | 10/2007 | Kawai et al. |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,390,309 B2 | 6/2008 | Dariush |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,628,766 B1 | 12/2009 | Kazerooni et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,770,842 B2 | 8/2010 | Benson |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,874,223 B2 | 1/2011 | Sugar et al. |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |

(56) References Cited

U.S. PATENT DOCUMENTS

| | | |
|---|---|---|
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |
| 7,981,068 B2 | 7/2011 | Thorgilsdottir et al. |
| 7,985,193 B2 | 7/2011 | Thorsteinsson et al. |
| 7,985,265 B2 | 7/2011 | Moser et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,142,370 B2 | 3/2012 | Weinberg et al. |
| 8,181,520 B2 | 5/2012 | Kadota et al. |
| 8,202,325 B2 | 6/2012 | Albrecht-Laatsch et al. |
| 8,287,477 B1 | 10/2012 | Herr et al. |
| 8,419,804 B2 | 4/2013 | Herr et al. |
| 8,551,184 B1 | 10/2013 | Herr |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0083528 A1 | 5/2004 | Stewart et al. |
| 2004/0088025 A1 | 5/2004 | Gesotti |
| 2004/0172097 A1 | 9/2004 | Brodard et al. |
| 2004/0181118 A1 | 9/2004 | Kochamba |
| 2004/0181289 A1 | 9/2004 | Bedard et al. |
| 2004/0255711 A1 | 12/2004 | Takenaka et al. |
| 2004/0261561 A1 | 12/2004 | Takenaka et al. |
| 2005/0007834 A1 | 1/2005 | Hidaka |
| 2005/0043614 A1 | 2/2005 | Huizenga et al. |
| 2005/0049652 A1 | 3/2005 | Tong |
| 2005/0059908 A1 | 3/2005 | Bogert |
| 2005/0070834 A1 | 3/2005 | Herr et al. |
| 2005/0085948 A1 | 4/2005 | Herr et al. |
| 2005/0155444 A1 | 7/2005 | Otaki et al. |
| 2005/0179417 A1 | 8/2005 | Takenaka et al. |
| 2005/0197717 A1 | 9/2005 | Ragnarsdottir et al. |
| 2005/0209707 A1 | 9/2005 | Phillips et al. |
| 2005/0228515 A1 | 10/2005 | Musallam et al. |
| 2005/0251079 A1 | 11/2005 | Carvey et al. |
| 2006/0004299 A1 | 1/2006 | Endo et al. |
| 2006/0004307 A1 | 1/2006 | Horst |
| 2006/0055358 A1 | 3/2006 | Ogawa et al. |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0135883 A1 | 6/2006 | Jonsson et al. |
| 2006/0173552 A1 | 8/2006 | Roy |
| 2006/0184280 A1 | 8/2006 | Oddsson et al. |
| 2006/0211956 A1 | 9/2006 | Sankai |
| 2006/0213305 A1 | 9/2006 | Sugar et al. |
| 2006/0214621 A1 | 9/2006 | Ogawa et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0156252 A1 | 7/2007 | Jonsson et al. |
| 2007/0162152 A1 | 7/2007 | Herr et al. |
| 2007/0233279 A1 | 10/2007 | Kazerooni et al. |
| 2007/0267791 A1 | 11/2007 | Hollander et al. |
| 2008/0039756 A1 | 2/2008 | Thorsteinsson et al. |
| 2008/0114272 A1 | 5/2008 | Herr et al. |
| 2008/0155444 A1 | 6/2008 | Pannese et al. |
| 2008/0161937 A1 | 7/2008 | Sankai |
| 2008/0234608 A1 | 9/2008 | Sankai |
| 2009/0030530 A1 | 1/2009 | Martin |
| 2009/0171469 A1 | 7/2009 | Thorsteinsson et al. |
| 2009/0192619 A1 | 7/2009 | Martin et al. |
| 2009/0222105 A1 | 9/2009 | Clausen |
| 2010/0004860 A1 | 1/2010 | Chernoguz et al. |
| 2010/0025409 A1 | 2/2010 | Hunter |
| 2010/0094188 A1 | 4/2010 | Goffer et al. |
| 2010/0113980 A1 | 5/2010 | Herr et al. |
| 2010/0114329 A1 | 5/2010 | Casler et al. |
| 2010/0174384 A1 | 7/2010 | Herr et al. |
| 2010/0174385 A1 | 7/2010 | Casler et al. |
| 2010/0179668 A1 | 7/2010 | Herr et al. |
| 2010/0312363 A1 | 12/2010 | Herr et al. |
| 2011/0082566 A1 | 4/2011 | Herr et al. |
| 2011/0105966 A1 | 5/2011 | Kazerooni et al. |
| 2011/0224804 A1 | 9/2011 | Clausen et al. |
| 2011/0245931 A1 | 10/2011 | Clausen et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2011/0295384 A1 | 12/2011 | Herr et al. |
| 2011/0295385 A1 | 12/2011 | Herr et al. |
| 2012/0209405 A1 | 8/2012 | Herr et al. |
| 2012/0259429 A1 | 10/2012 | Han et al. |
| 2012/0259430 A1 | 10/2012 | Han et al. |
| 2012/0259431 A1 | 10/2012 | Han et al. |
| 2012/0271433 A1 | 10/2012 | Galea et al. |
| 2012/0283845 A1 | 11/2012 | Herr et al. |
| 2013/0312483 A1 | 11/2013 | Herr et al. |

FOREIGN PATENT DOCUMENTS

| | | |
|---|---|---|
| EP | 1 534 117 | 6/2005 |
| JP | 2005-000500 | 1/2005 |
| WO | WO 1994/09727 A2 | 5/1994 |
| WO | WO 2003/003953 A1 | 1/2003 |
| WO | WO 03/068453 A2 | 8/2003 |
| WO | WO 2004/017872 A1 | 3/2004 |
| WO | WO 2004/019832 A2 | 3/2004 |
| WO | WO 2006/110895 | 10/2006 |
| WO | WO 2007/025116 A2 | 3/2007 |
| WO | WO 2009/011682 A1 | 1/2009 |
| WO | WO 2009/082249 | 7/2009 |

(56) References Cited

FOREIGN PATENT DOCUMENTS

| WO | WO 2010/025403 A1 | 3/2010 |
| WO | WO 2010/025409 | 3/2010 |
| WO | WO 2010/027968 A2 | 3/2010 |
| WO | WO 2011/005482 A2 | 1/2011 |

OTHER PUBLICATIONS

Abul-haj, C. and Hogan, N., Functional assessment of control systems for cybernetic elbow prostheses. Part I, Part II, IEEE Transactions on Biomedical Engineering, vol. 37, No. 11, Nov. 1990, Cambridge, MA, pp. 1037-1047.

Akazawa, K., et. al, Biomimetic EMG prosthesis-hand, Proceedings of the 18th Annual International Conference of the IEEE Engineering in Medicine and Biology Society, vol. 2, Oct. 1996, Amsterdam, Netherlands, pp. 535-536.

Aminian, Estimation of Speed and Incline of Walking Using Neural Network, IEEE Transactions on Biomedical Engineering, vol. 44, No. 3, Jun. 1995, pp. 743-746.

Anderson, F. and Pandy M., Dynamic optimization of human walking, Journal of Biomechanical Engineering, vol. 123, Oct. 2001, pp. 381-390.

Andrews, et al., Hybrid FES Orthosis incorporating closed loop control and sensory feedback, J. Biomed Eng., vol. 10, Apr. 1988, pp. 189-195.

Arakawa, T. and Fukuda, T., Natural motion generation of biped locomotion robot using hierarchical trajectory generation method consisting of GA, EP layers, Proceedings of the 1997 IEEE International Conference on Robotics and Automation, Apr. 1997, Albuquerque, NM, pp. 211-216.

Au, S. and Herr H., Initial experimental study on dynamic interaction between an amputee and a powered ankle-foot prosthesis, Workshop on Dynamic Walking: Mechanics and Control of Human and Robot Locomotion, May 2006, Ann Arbor, MI, p. 1.

Au, S., An EMG-position controlled system for an active ankle-foot prosthesis: an initial experimental study, Proc. of the 2006 IEEE International Conference on Rehabilitation Robotics, Jul. 2005, Chicago, IL, pp. 375-379.

Au, S., et al. An ankle-foot emulation system for the study of human walking biomechanics, Proc. of the 2006 IEEE Int. Conf. on Robotics and Automation, May 2006, Orlando, FL, pp. 2939-2945.

Au, S., et. al., Biomechanical design of a powered ankle-foot prosthesis, Proc. of the 2007 IEEE Int. Conf. on Rehabilitation Robotics, Jun. 2007, Noordwijk, Netherlands, pp. 298-303.

Au, S., et. al., Powered Ankle-foot Prosthesis Improves Walking Metabolic Economy, IEEE Trans. on Robotics, vol. 25, No. 1, Feb. 2009, pp. 51-66.

Au, S., et. al., Powered ankle-foot prosthesis to assist level-ground and stair-descent gaits, Neural Networks, vol. 21, No. 4, Mar. 2008, pp. 654-666.

Au., et. al., Powered Ankle-Foot Prosthesis for the Improvement of Amputee Ambulation, Proceedings of the 29th Annual International Conference of the IEEE, Aug. 2007, Lyon, France, pp. 3020-3026.

Barth, D.., et. al., Gait analysis and energy cost of below-knee amputees wearing six different prosthetic feet, Journal of Prosthetics & Orthotics, vol. 4, No. 2, Winter, 1992, pp. 63-75.

Baten, et al., Inertial Sensing in Ambulatory back load Estimation, 18 Annual International Conferences of IEEE Engineering in Medicine and Biology Society, Amsterdam 1996, pp. 497-498.

Bateni, H. and Olney S., Kinematic and kinetic variations of below-knee amputee gait, Journal of Prosthetics & Orthotics, vol. 14, No. 1, Mar. 2002, pp. 2-13.

Blaya et al., Adaptive control of a variable-impedance ankle-foot orthosis to assist drop-foot gait, IEEE Transactions on Neural Systems and Rehabilitation Engineering, vol. 12, No. 1, Mar. 2004, pp. 24-31.

Blaya, et al., Active Ankle Foot Orthoses (AAFO). http://www.ai.mit.edu. Artificial Intelligence Laboratory, Massachusetts Institute of Technology, Cambridge, Massachusetts. 2001. 3 pages.

Blaya, J.A., Force-Controllable Ankle Foot Orthosis (AFO) to Assist Drop Foot Gait, submitted to the Department of Mechanical Engineering,Massachusetts Institute of Technology, Cambridge, Massachusetts (Feb. 2003). 88 pages.

Blickhan, R., The spring-mass model for running and hopping, J of Biomech. Feb. 22, 1989, Great Britain, pp. 1217-1227.

Bortz, A New Mathematical Formulation for Strapdown Inertial Navigation, IEEE Transactions of Aerospace and Electronic Systems, vol. AES-7, No. 1, Jan. 1971, p. 61-66.

Bouten et al., Assessment of energy expenditure for physical activity using a triaxial accelerometer. Med Sci Sports Exerc. Dec. 1994;26(12):1516-23.

Bouten, A Triaxial Accelerometer and Portable Data Processing Unit for the Assessment of Daily Physical Activity, IEEE Transactions on Biomedical Engineering, vol. 44, No. 3, Mar. 1997, pp. 136-147.

Brockway, J., Derivation of formulae used to calculate energy expenditure in man, Human Nutrition Clinical Nutrition, vol. 41, Nov. 1987, pp. 463-471.

Brown, R., On the nature of the fundamental activity of the nervous centres: together with an analysis of the conditioning of rhythmic activity in progression, and a theory of the evolution of function in the nervous system, J Physiol, vol. 48,No. 1, Mar. 1914, pp. 18-46.

Chang, et al., Ischemic Colitis and Complications of Constipation Associated with the use of Alosetron Under a Risk Management Plan: Clinical Characteristics, Outcomes, and Incidences The American Journal of Gastronenterology, vol. 105, No. 4, Apr. 2010, pp. 866-875.

Chu, A., Kazerooni, H. and Zoss, A., On the Biomimetic Design of the Berkeley Lower Extremity Exoskeleton (BLEEX), Proceedings of the 2005 IEEE International Conference on Robotics and Automation, Apr. 2005, Barcelona, Spain, pp. 4356-4363.

Colborne, G. R., S. Naumann, P. E. Longmuir, and D. Berbrayer, Analysis of mechanical and metabolic factors in the gait of congenital below knee amputees, Am. J. Phys. Med. Rehabil., vol. 92, pp. 272-278, Oct. 1992.

Colgate, The control of dynamically interacting systems. MIT. Aug. 1988. 1-19.

Collins, et al., Controlled Energy Storage and Return Prosthesis Reduces Metabolic cost of Walking, ASB 29.sup.th Annual Meeting, Cleveland, Ohio, Jul. 31-Aug. 5, 2005, 1 page.

Collins, et al., Supporting Online Material for Efficient bipedal robots based on passive-dynamic walkers, Mechanical Engineering, University of Michigan, Feb. 2005, Ann Arbor, MI, pp. 1-8.

Crago P., et. al., New Control Strategies for neuroprosthetic systems, Journal of Rehabilitation Research and Development, vol. 33, No. 2, Apr. 1996, pp. 158-172.

Daley, M. A., Felix, G., Biewener, A. A., 2007. Running stability is enhanced by a proximo-distal gradient in joint neuromechanical control. J Exp Biol 210 (Pt 3), Nov. 2006, pp. 383-394.

Dapena, J. and McDonald, C., Three-dimensional analysis of angular momentum in the hammer throw, Med. Sci. in Sports Exerc., vol. 21, No. 2, Apr. 1989, pp. 206-220.

Davids et al., Disorders of Bone and Mineral Metabolism. Book reviews. J Ped Orthopaedics. 1992;12(6):815.

Dietz, V., Proprioception and locomotor disorders, Nat Rev Neurosci, vol. 3, Oct. 2002, pp. 781-790.

Dietz, V., Spinal Cord Pattern Generators for Locomotion, download Feb. 6, 2012, http://www.Clinph-journal.com/article/PIIS1388245703001202/fullt- ext, 12 pages.

Doerschuk, et. al., Upper extremity limb function discrimination using EMG signal analysis, IEEE Transactions on Biomedical Engineering. vol. 30., No. 1., Jan. 1983, pp. 18-28.

Doke, J., et. al., Mechanics and energetics of swinging the human leg, The Journal of Experimental Biology, vol. 208, Feb. 2005, pp. 439-445.

Dollar, et al., Lower Extremity Exoskeletons and Active Orthoses: Challenges and State-of-the-Art, IEEE Transcations on Robotics, vol. 24, No. 1, Feb. 2008, 15 pages.

Donelan, J., et. al. Simultaneous positive and negative external mechanical work in human walking, Journal of Biomechanics, vol. 35, Jan. 2002, pp. 117-124.

(56) References Cited

OTHER PUBLICATIONS

Donelan, J., et. al., Force regulation of ankle extensor muscle activity in freely walking cats, J Neurophysiol, vol. 101, No. 1, Nov. 2008, pp. 360-371.

Donelan, J., et. al., Mechanical work for step-to-step transitions is a major determinant of the metabolic cost of human walking, J. Exp. Biol., vol. 205, Dec. 2002, pp. 3717-3727.

Drake, C., Ankle & Foot Splints or Orthoses (AFOs), HemiHelp, Last updated Jun. 2009, 8 pages.

Drake, C., Ankle & Foot Splints or Orthoses, HemiHelp, Information Sheet 13 Last updated Jun. 2009, 5 pages.

Drake, Foot & Ankle Splints or Orthoses. HemiHelp Information Sheet, London, United Kingdom. Jun. 2009;1-5.

Eilenberg, M., A Neuromuscular-Model Based Control Strategy for Powered Ankle-Foot Prostheses, Masters Thesis, Massachusetts Institute of Technology, Cambridge, Mass., 2009.

Ekeberg, O. and Grillner, S., Simulations of neuromuscular control in lamprey swimming, Philos Trans R Soc Lond B Biol Sci, vol. 354, May 1999, pp. 895-902.

Ekeberg, O. and Pearson, K., Computer simulation of stepping in the hind legs of the cat: an examination of mechanisms regulating the stance-to-swing transition, J Neurophysiol, vol. 94, No. 6, Jul. 2005, pp. 4256-4268.

Endo, K., et. al., A quasi-passive model of human leg function in level-ground walking, Proc. of 2006 IEEE/RSJ International Conference on Intelligent Robots and Systems (IROS), Oct. 2006, Beijing, China, pp. 4935-4939.

Eppinger, S. Seering W., Three dynamic problems in robot force control, IEEE Transactions on Robotics and Automation, vol. 8, No. 6, Dec. 1992, pp. 751-758.

Esquenazi, A. and DiGiacomo, R., Rehabilitation After Amputation, Journ Am Podiatr Med Assoc, vol. 91, No. 1, Jan. 2001, pp. 13-22.

Farley, C. and McMahon, T., Energetics of walking and running: insights from simulated reduced-gravity experiments, The American Physiological Society, Dec. 1992, pp. 2709-2712.

Farry, K. A., et al., Myoelectric teleoperation of a complex robotic hand, IEEE Transactions on Robotics and Automation. vol. 12, No. 5, Oct. 1996, pp. 775-788.

Featherstone, R., 1987, Robot Dynamic Algorithms, Boston, Mass., Kluwer Academic Publishers, pp. 155-172.

Fisekovic et al., New controller for functional electrical stimulation systems, Medical Engineering & Physics vol. 23, 2001, pp. 391-399.

Fite, K., et. al., Design and Control of an Electrically Powered Knee Prosthesis, Proc. of 2007 IEEE 10th International Conference on Rehabilitation Robotics (ICORR), Jun. 2007, pp. 902-905.

Flowers, W. A Man-Interactive Simulator System for Above-Knee Prosthetic Studies, Ph.D. thesis, Massachusetts of Institute Technology, Department of Mechanical Engineering. Jul. 10, 1973.

Fod, A., et. al., Automated Derivation of Primitives for Movements Classification, Autonomous Robots, vol. 12, No. 1, Jan. 2002, pp. 39-54.

Foerster et al., Detection of posture and motion by accelerometry a validation study in ambulatory monitoring, Computer in Human Behavior, 1999, pp. 571-583.

Foxlin et al., Miniature 6-DOF inertial system for tracking HMDs, In SPIE vol. 3362, Helmet and Head-Mounted Displays III, AeroSense 98, Orlando, FL, Apr. 13-14, 1998, 15 pages.

Frigon, A. and Rossignol, S., Experiments and models of sensorimotor interactions during locomotion, Biol Cybern, vol. 95, No. 6, Nov. 2006, pp. 607-627.

Fujita K, et. al., Joint angle control with command filter for human ankle movement using functional electrical stimulation, Proc. of IEEE Ninth Annual Conference for the Engineering in Medicine and Biology Society, Nov. 1987, Boston, MA, pp. 1719-1720.

Fukuda, O. et al., A human-assisting manipulator teleoperated by EMG signals and arm motions, IEEE Transactions on Robotics and Automation. vol. 19, No. 2, Apr. 2003, pp. 210-222.

Gates, D., Characterizing ankle function during stair ascent, descent, and level walking for ankle prosthesis and orthosis design, Masters thesis, Boston University, 2004, pp. 1-82.

Geiritsen, K., et. al., Direct dynamics simulation of the impact phase in heel-toe running, J. Biomech., vol. 28, No. 6, Jun. 1995, Great Britain, pp. 661-668.

Geyer, H. and Herr H., A muscle-reflex model that encodes principles of legged mechanics predicts human walking dynamics and muscle activities, IEEE Transactions on Neural Systems and Rehabilitations Engineering, vol. 18, No. 3, Jun. 2010, pp. 263-273.

Geyer, H., et. al., Compliant leg behaviour explains the basic dynamics of walking and running, Proc. R. Soc. Cond. B 273, Aug. 2006, pp. 2861-2867.

Geyer, H., et. al., Positive force feedback in bouncing gaits?, Proceedings of Royal Society B-Biological Sciences, vol. 270, No. 1529, Aug. 2003, pp. 2173-2183, 2003.

Ghigliazza, R., et. al., A simply stabilized running model, SIAM J. Applied. Dynamical Systems, vol. 2, No. 2, May 2004, pp. 187-218.

Giszter et al., Convergent force fields organized in the frog's spinal cord. J Neurosci. Feb. 1993;13(2):467-91.

Godha, el al., Integrated GPS/INS System for Pedestrian Navigation in a Signal Degraded Environment, ION GNSS, Sep. 2006, Fort Worth, TX, pp. 1-14.

Goswami, A. and Kallem, V., Rate of change of angular momentum and balance maintenance of biped robots, Proceedings of the 2004 IEEE International Conference on Robotics and Automation, Apr. 2004, New Orleans, La., pp. 3785-3790.

Goswami, A., Postural stability of biped robots and the foot-rotation indicator (FRI) point, International Journal of Robotics Research, vol. 18, No. 6, Jun. 1999, pp. 523-533.

Graupe, D., et al., A microprocessor system for multifunctional control of upper-limb prostheses via myoelectric signal identification, IEEE Transaction on Automatic Control. vol. AC-23, vol. 4, Aug. 1978, pp. 538-544.

Gregoire, L., and et al, Role of mono- and bi-articular muscles in explosive movements, International Journal of Sports Medicine 5, 614-630. Dec. 1984. 301-305.

Grillner, S. and Zangger, P., On the central generation of locomotion in the low spinal cat, Exp Brain Res, vol. 34, No. 2, Jan. 1979, pp. 241-261.

Grimes, D. L., An active multi-mode above-knee prosthesis controller, Ph.D. Thesis, Massachusetts Institute of Technology, Jul. 20, 1979.

Gu, W., The Regulation of Angular Momentum During Human Walking, Undergraduate Thesis, Massachusetts Institute of Technology, Physics Department, Jun. 2003, pp. 2-48.

Gunther, M. and Ruder, H., Synthesis of two-dimensional human walking: a test of the A-model, Biol. Cybern., vol. 89, May 2003, pp. 89-106.

Gunther, M., et. al., Human leg design: optimal axial alignment under constraints, J. Math. Biol., vol. 48, Mar. 2004, pp. 623-646.

Hanafusa et al., A Robot Hand with Elastic Fingers and Its Application to Assembly Process, pp. 337-359, Robot Motion, Brady et al., MITPress, Cambridge, MA, 1982.

Hansen, A. H., Childress, D. S., Miff, S. C., Gard, S. A., Mesplay, K. P., The human ankle during walking: implication for the design of biomimetic ankle prosthesis, Journal of Biomechanics, vol. 37, No. 10, Oct. 2004, pp. 1467-1474.

Hashimoto et al., An instrumented compliant wrist using a parallel mechanism, Japan/USA Symposim on Flexible Automation, vol. 1, pp. 741-744, ASME, 1992.

Hayes et al., Leg Motion Analysis During Gait by Multiaxial Accelerometry: Theoretical Foundations and Preliminary Validations, Journal of Biomechanical Engineering, vol. 105, Aug. 1983, pp. 283-289.

Heglund, A Simple Design for a Force-Plat to Measure Ground Reaction Forces, J. exp. Biol., vol. 93, pp. 333-338, 1981.

Herr, H. and McMahon, T.,A trotting horse model, Int. J. Robotics Res., vol. 19, No. 6, Jun. 2000, pp. 566-581.

Herr, H. and Popovic, M., Angular momentum regulation in human walking, J. Exp. Biol., vol. 211, Feb. 2008, pp. 467-481.

(56) References Cited

OTHER PUBLICATIONS

Herr, H. and Wilkenfeld A., User-adaptive control of a magnetorheologicalprosthetic knee, Industrial Robot: An International Journal, vol. 30, No. 1, 2003, pp. 42-55.
Herr, H., et. al, A model of scale effects in mammalian quadrupedal running, J Exp Biol 205 (Pt 7), Apr. 2002, pp. 959-967.
Herr, New Horizons for Orthotic and Prosthetic Technology: Artificial Muscle for Ambulation. MIT Media Laboratory. 2004:1-9.
Heyn et al., The Kinematice of the Swing Phase Obtained from Accelerometer and Gyroscope Measurements, 18.sup.th Annual International Conference of the IEEE Engineering in Medicine and Biology Society, Nov. 1996, Amsterdam, Netherlands, pp. 463-464.
Hill, V., The heat of shortening and the dynamic constants of muscle, Proceedings of the Royal Society London B, vol. 126, No. 843, Oct. 1938, pp. 136-195.
Hirai, K., et al., The development of Honda humanoid robot, Proceedings on IEEE/RSJ International Conference on Intelligent Robots and Systems, May 1998, Leuven, Belgium, pp. 1321-1326.
Hitt, J., R. Bellman, M. Holgate, T. Sugar, and K. Hollander, The sparky (spring ankle with regenerative kinetics) projects: Design and analysis of a robotic transtibial prosthesis with regenerative kinetics, in Proc. IEEE Int. Conf. Robot. Autom.Orlando, Fla., pp. 1587-1596, Sep. 2007.
Hof. A., et. al., Calf muscle moment, work and efficiency in level walking; role of series elasticity, Journal of Biomechanics, vol. 16, No. 7, Sep. 1983, pp. 523-537.
Hofbaur, M. and Williams, B., Hybrid Diagnosis with Unknown Behavioral Modes, Proceedings of the 13.sup.th International Workshop on Principles of Diagnosis (DX02), May 2002, pp. 1-10.
Hofbaur, M. and Williams, B., Mode Estimation of Probabilistic Hybrid Systems, HSSC 2002, LNCS 2289, Mar. 25, 2002, pp. 253-266.
Hofmann, A., et. al., A Sliding Controller for Bipedal Balancing Using Integrated Movement of Contact and Non-Contact Limbs, Proceedings of the IEEE/RSJ International Conference on Intelligent Robots and Systems, Sep. 2004, Sendai, Japan, pp. 1952-1959.
Hofmann, A., et. al., Robust Execution of Bipedal Walking Tasks from Biomechanical Principles, Doctor of Philosophy at the Massachusetts Institute of Technology, Jan. 2006, 407 pages.
Hogan, N. and Buerger S., Impedance and Interaction Control, Robotics and Automation Handbook, CRC Press, Jun. 2004, pp. 19.1-19.24.
Hogan, N. (1976) A review of the methods of processing EMG for use as a proportional control signal. Biomedical Engineering. pp. 81-86.
Hogan, N., Impedance Control: An Approach to Manipulation, Dept. of Mechanical Engineering and Labortory of Manufacturing and Productivity, Massachusetts Institute of Technology, Cambridge MA, pp. 304-313, (Jun. 1984).
Hogan, N., Impedance Control: An Approach to Manipulation: Part I—Theory, Journal of Dynamic Systems, Measurement , and Control, vol. 107, Mar. 1985, pp. 1-7.
Hogan, N., Impedance Control: An Approach to Manipulation: Part II—Implementation, Journal of Dynamic Systems, Measurement , and Control, 107:8-16, (1985).
Hogan, N., Impedance Control: An Approach to Manipulation: Part III—Application, Journal of Dynamics Systems, Measurement, and Control, 107:17-24, (1985).
Hollander, K. W., T. G. Sugar, and D. E. Herring, Adjustable robotic tendon using a 'Jack Springs'.TM., Proceedings on IEEE International Conference on Rehabilitation Robotics, Chicago, pp. 113-118, Jun. 28, 2005.
Howard, Joint and Actuator Design for Enhanced Stability in Robotic Force Control, Ph.D. thesis, Massachusetts Inst. of Technology, Dept. of Aeronautics and Astronautics, Sep. 19, 1990.
Huang, H. and Chen. C., Development of a myoelectric discrimination system for a multi-degree prosthetic hand, Proceeding of the 1999 IEEE International Conference on Robotics and Automation, May 1999, Detroit, MI, pp. 2392-2397.
Huang, Q., Planning walking patterns for a biped robot, IEEE Transactions on Robotics and Automation, vol. 17, No. 3, Jun. 2001, pp. 280-289.
Hultborn, H., Spinal reflexes, mechanisms and concepts: from Eccles to Lundberg and beyond, Prog Neurobiol, vol. 78, Feb. 2006, pp. 215-232.
Ijspeert, A. J., 2008, Central pattern generators for locomotion control in animals and robots: a review, Neural Netw, vol. 21, No. 4, May 2008, pp. 642-653.
Ijspeert, A., et. al., From swimming to walking with a salamander robot driven by a spinal cord model, Science, vol. 315, No. 5817, Mar. 2007, pp. 1416-1420.
Isakower, Design Charts for Torsional Properties of Non-circular Shafts, Technical Report ARMID-TR-78001, ARRADCOM, MISD, DRDAR-MSA, Dover,NJ, Nov. 1978 . . . .
Ivashko, D., et. al, Modeling the spinal cord neural circuitry controlling cat hindlimb movement during locomotion, Neurocomputing, vol. 52-54, Mar. 2003, pp. 621-629.
Johansson, J., et al., A clinical comparison of variable damping and mechanically passive prosthetic knee devices, American Journal of Physical Medicine & Rehabilitation, vol. 84, No. 8, Aug. 2005, pp. 563-575.
Johnson, C. and Lorenz R., Experimental identification of friction and its compensation in precise, position controlled mechanisms, IEEE Trans. on Industry Applications, vol. 28, No. 6, Dec. 1992, pp. 1392-1398.
Jonic S, et. al., Three machine learning techniques for automatic determination of rules to control locomotion, IEEE Trans Biomed Eng, vol. 46, No. 3, Mar. 1999, pp. 300-310.
Kadaba, M., et. al., Measurement of lower extremity kinematics during level walking, J. Orthop. Res., vol. 8, May 1990, pp. 383-392.
Kadaba, M., et. al., Repeatability of kinematic, kinetic, and electromyographic data in normal adult gait, J. Orthop. Res., vol. 7, Nov. 1989, pp. 849-860.
Kajita, K., et. al., Biped walking on a low friction floor, Proceedings of the 2004 IEEE/RSJ International Conference on Intelligent Robots and Systems, Oct. 2004, Sendai, Japan., pp. 3546-3551.
Kajita, S., et. al., A Hop towards Running Humanoid Biped, Proceedings of the 2004 IEEE International Conference on Robotics and Automation, Apr. 2004, New Orleans, La., pp. 629-635.
Kajita, S., et. al., Resolved Momentum Control: Humanoid Motion Planning based on the Linear and Angular Momentum, Proceedings of the 2003 IEEE/RSJ International Conference on Intelligent Robots and Systems, Oct. 2003, Las Vegas, Nev., pp. 1644-1650.
Kaneko, K., et al., Humanoid robot HRP-2, Proc. IEEE Int. Conf. on Robotics and Automation, Apr. 2004, New Orleans, La., pp. 1083-1090.
Kapti, A. and Yucenur M., Design and control of an active artificial knee joint, Mechanism and Machine Theory, vol. 41, Apr. 2006, pp. 1477-1485.
Katic, D. and Vukobratovic, M., Survey of intelligent control techniques for humanoid robots, Journal of Intelligent and Robotics Systems, vol. 37, Jun. 2003, pp. 117-141.
Kerrigan, D, et. al., A refined view of thedeterminants of gait: significance of heel rise, Arch. Phys. Med. Rehab., vol. 81, Aug. 2000, pp. 1077-1080.
Kerrigan, D, et. al., Quantification of pelvic rotation as a determinant of gait, Arch. Phys. Med. Rehab., vol. 82, Feb. 2001, pp. 217-220.
Khatib, O., et. al., Coordination and decentralized cooperation of multiple mobile manipulators, Journal of Robotic Systems, vol. 13, No. 11, Nov. 1996, pp. 755-764.
Khatib, O., et. al., Whole body dynamic behavior and control of human-like robots, International Journal of Humanoid Robotics, vol. 1, No. 1, Mar. 2004, pp. 29-43.
Kidder, et al., A System for the Analysis of Foot and Ankle Kinematics During Gait, IEEE Transactions on Rehabilitation Engineering, vol. 4, No. 1, Mar. 1996, pp. 25-32.
Kim, et al., Realization of Dynamic Walking for the Humaniod Robot Platform KHR-1, Advanced Robotics, vol. 18, No. 7, pp. 749-768, (2004).

(56) References Cited

OTHER PUBLICATIONS

Kirkwood C, et. al., Automatic detection of gait events: a case study using inductive learning techniques., J Biomed Eng, vol. 11, Nov. 1989, pp. 511-516.
Kitayama, I., Nakagawa N, Amemori K, A microcomputer controlled intelligent A/K prosthesis, Proceedings of the 7th World Congress of the International Society for Prosthetics and Orthotics, Chicago. Jun. 28, 1992.
Klute et al., Powering Lower Limb Prosthestics with Muscle-Like Actuators, Abstract in: Proceeding of the 1st Annual Meeting of the VA Rehabilitation Research and Development Service, Enabling Veterans: Meeting the Challenge of Rehabilitation inthe Next Millennium, Washington, D.C., Oct. 1-3, 1998, p. 52.
Klute et al.,Variable Stiffness Prosthesis for Transtibial Amputees. Dept of Veteran Affairs, Seattle, WA USA, 2005. 2 pages.
Klute, et al., Artificial Muscles: Actuators for Biorobotic Systems, The International Journal of Robotics Research, vol. 21, No. 4, Apr. 2002, pp. 295-309.
Klute, et al., Artificial Tendons: Biomechanical Design Properties for Prosthetic Lower Limbs, Chicago 2000 World Congress on Medical Physics and Biomedical Engineering, Chicago on Jul. 24-28, 2000, 4 pages.
Klute, et al., Lower Limb Prostheses Powered by Muscle-Like Pneumatic Actuator, Submitted to Oleodinamica e Pneumatica, Publishe Tecniche Nuove, Milamo, Italy, Mar. 15, 2000, 6 pages.
Klute, et al., McKibben Artificial Muscles: Pneumatic Actuators with Biomechanical Intelligence, IEEE/ASME 1999 Inernational Conference on Advanced Intelligent Mechatronics, Atlanta, GA, Sep. 19-22, 1999, pp. 221-226.
Klute, et al., Muscle-Like Pneumatic Actuators for Below-Knee Prostheses, Actuator2000:7th International Conference on New Actuators, Bremen, Germany on Jun. 9-21, 2000, pp. 289-292.
Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.
Klute, et al., Intelligent Transtibial Prostheses with Muscle-Like Actuators,: 2002 American Physiological Society Intersociety Meeting: The Power of Comparative Physiology: Evolution, Integration, and Applied, 1 page.
Klute, G., et. al., Mechanical properties of prosthetic limbs adapting to the patient, Journal of Rehabilitation Research and Development, vol. 38, No. 3, May 2001, pp. 299-307.
Koganezawa, K. and Kato, I., Control aspects of artificial leg, IFAC Control Aspects of Biomedical Engineering, 1987, pp. 71-85.
Kondak, K. and Hommel, G., Control and online computation of stable movement for biped robots, Proc. of the 2003 IEEE/RSJ International Conference on Intelligent Robots and Systems (IROS), Oct. 2003, Las Vegas, Nev., pp. 874-879.
Kostov A., et. al., Machine learning in control of functional electrical stimulation (FES) systems for locomotion, IEEE Trans on Biomed Eng, vol. 42, No. 6, Jun. 1995, pp. 541-551.
Kuo, A., A simple model of bipedal walking predicts the preferred speed-step length relationship, Journal of Biomechanical Engineering, vol. 123, Jun. 2001, pp. 264-269.
Kuo, A., Energetics of actively powered locomotion using the simplest walking model, Journal of Biomechanical Engineering, vol. 124, Feb. 2002, pp. 113-120.
LaFortune, Three-Dimensional Acceleration of the Tibia During Walking and Running, J. Biomechanics, vol. 24, No. 10, 1991, pp. 877-886.
LeBlanc, M. and Dapena, J., Generation and transfer of angular momentum in the javelin throw, Presented at the 20th annual meeting of the American Society of Biomechanics, Oct. 1996, Atlanta, Ga., pp. 17-19.
Lee et al., activity and Location recognition Using Wearable Sensors, Pervasive Computing, Jul.-Sep. 2002, pp. 24-32.
Li et al., (Jun. 25, 2006) Research and development of the intelligently-controlled prosthetic ankle joint. Proc. of IEEE Int. Conf. on Mechatronics and Automation. Luoyang, China, pp. 1114-1119.

Light, et. al., Skeletal Transients on Heel Strike in Normal Walking With Different Footwear. J. Biomechanics vol. 13, pp. 477-480.
Liu, X., Low, K. H., Yu, H. Y., (2004) 'Development of a Lower Extremity Exoskeleton for Human performance Enhancement', IEEE Conf. on Intelligent Robots and Systems, Sendai, Japan.
Lloyd R. and Cooke C., Kinetic changes associated with load carriage using two rucksack designs, Ergonomics, vol. 43, No. 9, Sep. 2000, pp. 1331-1341.
Luinge, Inertial Sensing of Human Movement, Twente University Press, ISBN 9036518237, 2002, pp. 1-80.
Lundberg, A., Oct. 19, 1968. Reflex control of stepping. In: The Nansen memorial lecture V, Oslo: Universitetsforlaget, 5-42.
Macfarlane, P., Gait comparisons for below-knee amputees using a flex-foot versus a conventional prosthetic foot, Journal of Prosthetics & Orthotics, vol. 3, No. 4, Summer, 1991, pp. 150-161.
Maganaris, C., Force-length characteristics of in vivo human skeletal muscle, Acta Physiol. Scand., vol. 172, Aug. 2001, pp. 279-285.
Maganaris, C., Force-length characteristics of the in vivo human gastrocnemius muscle, Clin. Anat., vol. 16, May 2003, pp. 215-223.
Martens, W.L.J., Exploring the Information Content and Some Applications of Body Mounted Piezo-Resistive Accelerometers, in: P.H. Veltink and R.C. van Lummel (eds.), Dynamic Analysis using Body Fixed Sensors, ISBN 90-9007328-0, 1994, pp. 8-11.
Maufroy, C., Towards a general neural controller for quadrupedal locomotion, Neural Netw, vol. 21, No. 4, Apr. 2008, pp. 667-681.
Mayagoitia R., et al., Accelerometer and rate gyroscope measurement of kinematics: an inexpensive alternative to optical motion analysis systems, Journal of Biomechanics, vol. 35, Apr. 2002, pp. 537-542.
McFadyen et al., An integrated biomechanical analysis of normal stair ascent and descent. J Biomech. 1988;21(9):733-44.
McGeer T., Passive Dynamic Walking, International Journal of Robotics, vol. 9, No. 2, May 1988, pp. 62-82.
McGeer, T., Principles of walking and running, Advances in Comparative and Environmental Physiology, vol. 11, Ch. 4, Apr. 1992, pp. 113-139.
McIntosh, A., et. al., Gait dynamics on an inclined walkway, Journal of Biomechanics, vol. 39, Sep. 2005, pp. 2491-2502.
McMahon, T., The mechanics of running: how does stiffness couple with speed?, J. of Biomecb., vol. 23, 1990, pp. 65-78.
McMahon, T., et. al., Groucho Running, Journal of Applied Physiology, vol. 62, No. 6, Jun. 1987, pp. 2326-2337.
Minassian, K., et. al., Human lumbar cord circuitries can be activated by extrinsic tonic input to generate locomotor-like activity, Hum. Mov. Sci., vol. 26, Mar. 2007, pp. 275-295.
Mochon, S., et. al., Ballistic walking, Journal of Biomechanics, vol. 13, Dec. 1980, pp. 49-57.
Moe-Nilssen, A new method for evaluating motor control in gait under real-life environmental conditions, Part 2: Gait analysis, Clinical biomechanics, vol. 13, 1998, pp. 328-335.
Molen, N., Energy/speed relation of below-knee amputees walking on motor-driven treadmill, Int. Z. Angew. Physio, vol. 31, Mar. 1973, pp. 173.
Morris, Accelerometry—A Technique for the Measurement of Human Body Movements, J. Biomechanics, vol. 6, Nov. 1973, pp. 729-736.
Muraoka, T., et. al, Muscle fiber and tendon length changes in the human vastus lateralis during slow pedaling, J. Appl. Physiol., vol. 91, Nov. 2001, pp. 2035-2040.
Nakagawa A., Intelligent Knee Mechanism and the Possibility to Apply the Principle to the Other Joints, Proceedings of the 20.sup.th Annual International Conference of the IEEE Engineering in Medicine and Biology Society, Vo. 20, No. 5, Oct. 1998,pp. 2282-2287.
Neal R. and Hinton G., A view of the EM algorithm that justifies incremental, sparse, and other variants, In Michael I. Jordan (editor), Learning in Graphical Models, 1999, Cambridge, MA, pp. 1-14.
Ng, et al., Fuzzy Model Identification for Classification of Gait Events in Paraplegics, IEEE Transactions on Fuzzy Systems, vol. 5, No. 4, Nov. 1997, pp. 536-544.
Nielsen, D., et. al., Comparison of energy cost and gait efficiency during ambulation in below-knee amputees using different prosthetic feet—a preliminary report, Journal of Prosthetics & Orthotics, vol. 1, No. 1, 1989, pp. 24-29.

(56) References Cited

OTHER PUBLICATIONS

Oda et al., In Vivo Length-Force Relationships on Muscle Fiber and Muscle Tendon Complex in the Tibialis Anterior Muscle. Int. J. Sport and Health Sci. 2005;3:245-252.

Ogihara, N. and Yama7aki, N., Generation of human bipedal locomotion by a bio-mimetic neuro-musculo-skeletal model, Biol Cybern, vol. 84, No. 1, Jan. 2001, pp. 1-11.

Palmer, M., Sagittal plane characterization of normal human ankle function across a range of walking gait speeds, Master's Thesis, MIT, Feb. 2002, Cambridge, MA, pp. 1-71.

Paluska, D. and Herr, H., Series Elasticity and Actuator Power Output, Proceedings of the 2006 IEEE International Conference on Robotics and Automation, May 2006, Orlando, FL, pp. 1830-1833.

Paluska, D., and Herr, H., The effect of series elasticity on actuator power and work output: implications for robotic and prosthetic joint design, Robotics and Autonomous Systems, vol. 54, Jun. 2006, pp. 667-673.

Pang, M., et. al., The initiation of the swing phase in human infant stepping: importance of hip position and leg loading, J Physiol, vol. 528, No. 2, Oct. 2000, pp. 389-404.

Pasch, K. A., and W. P. Seering, On the drive systems for high performance machines, AMSE J.Mechanisms, Transmissions, and Automation in Design vol. 106, pp. 102-108, Mar. 1984.

Paul, C., et. al., Development of a human neuro-musculo-skeletal model for investigation of spinal cord injury, Biol Cybern, vol. 93, No. 3, Aug. 2005, pp. 153-170.

Pearson, K., Generating the walking gait: role of sensory feedback, Prog Brain Res, vol. 143, 2004, pp. 123-129.

Pearson, K., et. al., Assessing sensory function in locomotor systems using neuro-mechanical simulations, Trends Neurosci, vol. 29, No. 11, Nov. 2006, pp. 625-631.

Perry, Gait Analysis: Normal and Pathological Function, New Jersey: SLACK Inc.; 1992, Book Review, 1 page.

Perry, J. and S. Shanfield, Efficiency of dynamic elastic response prosthetic feet, Journal of Rehabilitation Research and Development, vol. 30, No. 1, 1993 pp. 137-143.

Petrofsky et al., Feedback Control System for Walking in Man, Comput. Biol. Med., vol. 14, No. 2, Mar. 1984, pp. 135-149.

Pfeffer et al., Experiments with a Dual-Armed, Cooperative, Flexible-Drivetrain Robot System, Proc. 1993 IEEE Int. Conf. on Robotics & Automation, vol. 3, pp. 601-608, May 5, 1993 . . . .

Popovic D., et al., Control Aspects of Active Above-Knee Prosthesis, Int. Journal Man-Machine Studies, (1991) 35, pp. 751-767.

Popovic, D., Control of Movement for the Physically Disabled, Springer-Verlag London Limited, May 2000, pp. 270-302.

Popovic, et al., Gait Identification and Recognition Sensor, Proceedings of 6th Vienna International Workshop on Functional Electrostimulation, Sep. 1998, pp. 1-4.

Popovic, M. and Herr, H., Global Motion Control and Support Base Planning, Proceedings of the IEEE/RSJ International Conference on Intelligent Robots and Systems, Aug. 2005, Alberta, Canada, pp. 1-8.

Popovic, M., Angular Momentum Primitives for Human Walking: Biomechanics and Control, Proc. of the 2004 IEEE/RSJ International Conference on Intelligent Robots and Systems, Sep. 2004, Sendai, Japan., pp. 1685-1691.

Popovic, M., et. al., Angular Momentum Regulation during human walking: Biomechanics and Control, Proceedings of the 2004 IEEE International Conference on Robotics and Automation, Apr. 2004, New Orleans, LA, pp. 2405-2411.

Popovic, M., et. al., Ground Reference Points in Legged Locomotion: Definitions, Biological Trajectories and Control Implications, International Journal of Robotics Research, Dec. 2006, pp. 79-104.

Popovic, M., et. al., Zero spin angular momentum control: definition and applicability, Proceedings of the IEEE-RAS/RSJ International Conference on Humanoid Robots, Nov. 2004, Los Angeles, CA, pp. 1-16.

Popovic, M.B., W. Gu and H. Herr, Conservation of Angular Momentum in Human Movement, MIT AI Laboratory—Research Abstracts, Sep. 2002. pp. 231-232, 2002.

Pratt, G. and Williamson M., Series elastic actuators, Proceedings on IEEE/RSJ International Conference on Intelligent Robots and Systems, Jan. 1995, Pittsburgh, PA, pp. 399-406.

Pratt, G., Legged Robots: What's New Since Raibert, IEEE Robotics and Automation Magazine, Research Perspectives, Sep. 2000, pp. 15-19.

Pratt, G., Low Impedance Walking Robots, Integ. and Comp. Biol., vol. 42, Feb. 2002, pp. 174-181.

Pratt, J., et. al., The RoboKnee: An Exoskeleton for Enhancing Strength and Endurance During Walking, IEEE Conf. on Robotics and Automation, Apr. 2004, New Orleans, LA, pp. 2430-2435.

Prochazka, A. and Yakovenko, S., The neuromechanical tuning hypothesis, Prog Brain Res, vol. 165, Oct. 2007, pp. 255-265.

Prochazka, A., et. al., Positive force feedback control of muscles, J. of Neuro-phys., vol. 77, Jun. 1997, pp. 3226-3236.

Prochazka, A., et. al., Sensory control of locomotion: reflexes versus higher-level control, Adv Exp Med Biol, vol. 508, 2002, pp. 357-367.

Raibert, M., Legged Robots that Balance, The MIT Press, Nov. 1986, Cambridge, MA, p. 89.

Rassier, D., et. al., Length dependence of active force production in skeletal muscle, Journal of Applied Physiology, vol. 86, Issue 5, May 1999, pp. 1455-1457.

Reitman, et. al., Gait analysis in prosthetics: opinions, ideas and conclusions, Prosthetics and Orthotics International, 2002, 26, 50-57.

Riener, R., et. al., Stair ascent and descent at different inclinations, Gait Posture, vol. 15, Feb. 2002, pp. 32-44.

Robinson, D., Design and an analysis of series elasticity in closed-loop actuator force control, Ph.D. Thesis, MIT, Jun. 2000, Cambridge, MA, pp. 1-123.

Robinson, D., Series elastic actuator development for a biomimetic walking robot, Proceedings of IEEE/ASME International Conference on Advanced Intelligent Mechatronics, Sep. 1999, pp. 561-568.

Rosen, J., et al., A myosignal-based powered exoskeleton system, IEEE Transactions on Systems, Man, and Cybernetics—Part A: Systems and Humans, vol. 31, No. 3, May 2001, pp. 210-222.

Ruina, A., et. al., A collisional model of the energetic cost of support work qualitatively explains leg sequencing in walking and galloping, pseudo-elastic leg behavior in running and the walk-to-run transition, Journal of Theoretical Biology,vol. 237, Issue 2, Jun. 2005, pp. 170-192.

Rybak et al., Modelling spinal circuitry involved in locomotor pattern generation: insights from the effects of afferent stimulation. J Physiol. Dec. 1, 2006;577(Pt 2):641-58. Epub Sep. 28, 2006.

Rybak, I., et. al., Modelling spinal circuitry involved in locomotor pattern generation: insights from deletions during fictive locomotion, J Physiol, vol. 577 (Pt 2), Dec. 2001, 617-639.

Sanderson, D., et. al., Lower extremity kinematic and kinetic adaptations in unilateral below-knee amputees during walking, Gait and Posture, vol. 6, No. 2, Oct. 1997, pp. 126-136.

Sanger, T., Human arm movements described by a low-dimensional superposition of principal component, Journal of NeuroScience, vol. 20, No. 3, Feb. 2000, pp. 1066-1072.

Saranli, U., RHex: A simple and highly mobile hexapod robot, Int. Jour. Rob. Res., vol. 20, No. 7, Jul. 2001, pp. 616-631.

Sarrigeorgidis K. and Kyriakopoulos K., Motion control of the N.T.U.A. robotic snamek on a planar surface, Proc. of the 1998 IEEE International Conference on Robotics and Automation, May 1998, pp. 2977-2982.

Schaal, S. and Atkeson, C., Constructive incremental learning from only local information, Neural Computation, vol. 10, No. 8, Nov. 1998, pp. 2047-2084.

Schaal, S., Is imitation learning the route to humanoid robots? Trends in Cognitive Sciences, vol. 3, Jun. 1999, pp. 233-242.

Scott, S. and Winter, D., Biomechanical model of the human foot: kinematics and kinetics during the stance phase of walking, J. Biomech., vol. 26, No. 9, Sep. 1993, 1091-1104.

Sekine et al., Classification of waist-acceleration signals in a continuous walking record, Medical Engineering & Physics, vol. 22, 2000, pp. 285-291.

(56) References Cited

OTHER PUBLICATIONS

Sentis, L. and O. Khatib, Task-Oriented Control of Humanoid Robots Through Prioritization, IEEE-RAS/RSJ International Conference on Humanoid Robots, Nov. 2004, Santa Monica, CA, pp. 1-16.
Seyfarth, A., Swing-leg retraction: a simple control model for stable running, J. Exp. Biol., vol. 206, Aug. 2003, pp. 2547-2555.
Seyfarth, A., et. al., A movement criterion for running, J. of Biomech., vol. 35, May 2002, pp. 649-655.
Seyfarth, A., et. al., Stable operation of an elastic three-segmented leg, Biol.Cybern., vol. 84, 2001, pp. 365-382.
Sin et al., Significance of non-level walking on transtibial prosthesis fitting with particular reference to the effects of anterior-posterior alignment, Journal of Rehabilitation Research and Development, vol. 38, No. 1, Jan./Feb. 2001, p. 1-6.
Sinkjaer, T., et. al., Major role for sensory feedback in soleus EMG activity in the stance phase of walking in man, J Physiol, vol. 523, No. 3, Mar. 2000, 817-827.
Skinner, H. and Effeney D., Gait analysis in amputees, Am J Phys Med, vol. 64, Apr. 1985, pp. 82-89.
Smidt et al., An Automated Accelerometry System for Gait Analysis, J. Biomechanics, vol. 10, 1977, pp. 367-375.
Srinivasan, M., Energetics of legged locomotion: Why is total metabolic cost proportional to the cost of stance work, Proc. on ISB XXth Congress and the American Society of Biomechanics Annual Meeting, Jul. 2003, Cleveland, OH, pp. 829.
Stepien, J., et al., Activity Levels Among Lower-Limb Amputees: Self-Report Versus Step Activity Monitor, Arch. Phys. Med. Rehabil., vol. 88, No. 7, Jul. 2007, pp. 896-900.
Sugano et al., Force Control of the Robot Finger Joint equipped with Mechanical Compliance Adjuster, Proc. of the 1992 IEEE/RSJ Int. Conf. on Intell. Robots & Sys., Jul. 1992, pp. 2005-2013.
Sugihara, T., et. al., Realtime Humanoid Motion Generation through ZMP Manipulation based on Inverted Pendulum Control, Proceedings of the 2002 IEEE International Conference on Robotics and Automation, May 2002, Washington, DC, pp. 1404-1409.
Sup, F., Design and Control of a Powered Transfemoral Prosthesis, The International Journal of Robotics Research, vol. 27, No. 2, Feb. 2008, pp. 263-273.
Taga, G., A model of the neuro-musculo-skeletal system for human locomotion, Biol. Cybern., vol. 73, No. 2, Jul. 1995, pp. 97-111.
Takayuki Biped Locomotion using Multiple Link Virtual Inverted Pendulum Model, Publication of Electronics Information and Systems Society, vol. 120, No. 2, Feb. 2000, 8 pages.
Thoroughman, K. and R. Shadmehr, Learning of action through adaptive combination of motor primitives, Nature, vol. 407, Oct. 2000, pp. 742-747.
Tomovic R. et al., A Finite State Approach to the Synthesis of Bioengineering Control Systems, IEEE Transations on Human Factors in Electronics, vol. 7, No. 2, Jun. 1966, pp. 65-69.
Tong et al., Virtual artificial sensor technique for functional electricial stimulation, Medical Engineering & Physics, vol. 20, 1998, pp. 458-468.
Tong, et al., A Practical Gait Analysis System Using Gyroscopes, Medical Engineering & Physics, vol. 21, Mar. 1999, pp. 87-94.
Turker, K., Electromyography: some methodological problems and issues, Physical Therapy, vol. 73, No. 10, Oct. 1993, pp. 698-710.
van den Bogert, A., Exotendons for assistance of human locomotion, Biomedical Engineering Online, Oct. 2003, pp. 1-8.
van den Bogert, et al. A Method for Inverse Dynamic Analysis Using Accelerometry, Journal Biomechanics, vol. 29, No. 7, 1996, pp. 949-954.

van der Kooij et al., A multisensory integration model of human stance control, Biological Cybernetics, 1999, pp. 299-308.
Veltink P., et al., The Feasibility of Posture and Movement Detection by Accelerometry, D-7803-1377-I/93, IEEE, Oct. 1993, pp. 1230-1231.
Veltink, Dection of Static and Dynamic Activities Using Uniaxial Accelerometers, IEEE. Transactions on Biomedical Engineering, vol. 4. No. 4, Dec. 1996, pp. 375-385.
Vukobratovic M. and Juricic, D., Contributions to the synthesis of biped gait, IEEE Transactions on Biomedical Engineering, vol. BME-16, No. 1, Jan. 1969, pp. 1-6.
Vukobratovic M. and Stepanenko J., Mathematical models of general anthropomorphic systems, Mathematical Biosciences, vol. 17, Aug. 1973, pp. 191-242.
Walsh, C., Biomimetic Design of an Under-Actuated Leg Exoskeleton for Load-Carrying Augmentation, Master's Thesis, MIT, Feb. 2006, pp. 1-94.
Waters, RL., Energy cost of walking amputees: the influence of level of amputation, J Bone Joint Surg., vol. 58, No. 1, Jan. 1976, pp. 42-46.
Wilkenfeld, A. J., Biologically inspired auto adaptive control of a knee prosthesis, Ph.D. Thesis, Massachusetts Institute of Technology, Oct. 23, 2000.
Wilkenfeld, A., An Auto-Adaptive External Knee Prosthesis, Artificial Intelligence Laboratory, MIT, Sep. 2000, Cambridge, MA, pp. 1-3.
Willemsen A., et al., Automatic Stance—Swing Phase Detection from Accelerometer Data for Peroneal Nerve Stimulation, IEEE Transactions on Human Factors in Electronics, vol. 37, No. 12, Dec. 1990, pp. 1201-1208.
Willemsen A., et al., Real-Time Gait Assessment Utilizing a New Way of Accelerometry, Journal of Biomechanics, vol. 23, No. 8, 1990, pp. 859-863.
Williams, B., Mode Estimation of Model-based Programs: Monitoring Systems with Complex Behavior, Proceedings of the International Joint Conference on Artificial Intelligence, Aug. 2001, Seattle, WA, pp. 1-7.
Williamson, M., Series Elastic Actuators, Artificial Intelligence Laboratory, MIT, Jan. 1995, Cambridge, MA, pp. 1-74.
Winter, D, and Robertson D., Joint torque and energy patterns in normal gait, Biol. Cybem., vol. 29, May 1978, pp. 137-142.
Winter, D. A, Energy generation and absorption at the ankle and knee during fast, natural, and slow cadences, Clinical Orthopedics and Related Research, vol. 175, May 1983, pp. 147-154.
Winter, D. and Sienko S., Biomechanics of below-knee amputee gait, Journal of Biomechanics, vol. 21, No. 5, Aug. 1988, pp. 361-367.
Wisse, M., Essentails of Dynamic Walking, Analysis and Design of two-legged robots, Phd Thesis, Technical University of Delft, 2004, pp. 1-195.
Woodward et al., Skeletal Accelerations measured during different Exercises, Proceedings of the Institution of Mechanical Engineers, Part H: Journal of Engineering in Medicine, vol. 207, Jun. 1993, pp. 79-85.
Wu, The Study of Kinematic Transients in Locomotion Using the Integrated Kinematic Sensor, IEEE Transactions on Rehabilitation Engineering, vol. 4, No. 3, Sep. 1996, p. 193-200.
Yakovenko, S., et. al., Contribution of stretch reflexes to locomotor control: a modeling study, Biol Cybern, vol. 90, No. 2, Jan. 2004, pp. 146-155.
Yun X., Dynamic state feedback control of constrained robot manipulators, Proc. of the 27th conference on Decision and Control, Dec. 1988, pp. 622-626.
Zlatnik, D., et. al., Finite-state control of a trans-femoral prosthesis, IEEE Trans. on Control System Technology, vol. 10, No. 3, May 2002, pp. 408-420.

| PHASE | 1. CONTROLLED PLANTAR FLEXION 102 | 2. CONTROLLED DORSIFLEXION 106 | 3. POWERED PLANTAR FLEXION 110 | 4. EARLY SWING 114 | 5. LATE SWING 118 |
|---|---|---|---|---|---|
| | \multicolumn{3}{c}{STANCE} | \multicolumn{2}{c}{SWING} |
| % OF CYCLE | \multicolumn{3}{c}{60%} | \multicolumn{2}{c}{40%} |
| INITIATING EVENT | FOOT-STRIKE | FOOT-FLAT | MAXIMUM DORSIFLEXION | TOE-OFF | VERTICAL ANKLE VELOCITY IS APPROXIMATELY ZERO |
| FUNCTION | IMPEDANCE (SPRING-DOMINATED) | TORQUE SOURCE + NONLINEAR IMPEDANCE | TORQUE SOURCE + IMPEDANCE | POSITION CONTROL | LINEAR SPRING |

FIG. 1

CONTROLLING TORQUE IN A PROSTHESIS OR ORTHOSIS BASED ON A DEFLECTION OF SERIES ELASTIC ELEMENT

CROSS REFERENCE TO RELATED APPLICATIONS

This application is a continuation of U.S. patent application Ser. No. 13/079,571 filed Apr. 4, 2011 which claims the benefit of U.S. Provisional Applications 61/320,991 filed Apr. 5, 2010, 61/422,873 filed Dec. 14, 2010, and 61/432,083 filed Jan. 12, 2011, each of which is incorporated herein by reference.

BACKGROUND

US published patent applications 2010/0174384 ("the '384 application") and 2006/0249315, each of which is incorporated herein by reference, describe that the gait cycle for walking can be divided into five phases: controlled plantarflexion, controlled dorsiflexion (CD), powered plantarflexion (PP), early swing, and late swing, as depicted in FIG. 1.

The '384 application also discloses a number of embodiments of lower-extremity prosthetic and orthotic systems in which the reflex torque generation during PP is achieved via non-linear, positive feedback between the series elastic element (SEE) motor torque and ankle torque. More specifically, the reflex action involves behaving like a non-linear spring during CD and like a torque source during PP. This reflex action can be implemented by driving the motor using the following equation:

$$\text{Motor Torque} = pff \times (\text{normalized\_Torque})^n \quad \text{Eq. 1}$$

Where, pff is the power control gain tuned for high walking speed; normalized_Torque is the ankle torque, $\Gamma_A$, normalized by a torque, $\Gamma_0$, (strongly related to users' weight); n is the power exponent, typically in the range of between 3 and 5 for level-ground walking. Note that pff has units of N-m, and the value of pff controls the magnitude of the level of the torque reflex during fast walking. Once the desired motor torque is determined, the drive current can be computed based on the equation Motor Current=Motor Torque/kt, where kt is the motor torque constant. While using Equation 1 does provide good results, the results provided by the control approach described below are significantly better.

SUMMARY OF THE INVENTION

One aspect of the invention is directed to an ankle-foot prosthesis or orthosis apparatus. The apparatus includes a shank member and a foot member that is operatively configured with respect to the shank member so as to supporting walking and permit the foot member to plantarflex and dorsiflex with respect to the shank member. A motor is configured to plantarflex the foot member with respect to the shank member, and a series elastic element is connected between at least one of (a) the motor and the shank member and (b) the motor and the foot member. There is at least one first sensor having an output from which a walking speed of an upcoming step can be predicted, and at least one second sensor having an output from which ankle torque can be determined. The apparatus also includes a controller configured to control the motor's torque, based on the output of the at least one first sensor and the at least one second sensor, so that the motor's torque for slow walking speeds is lower than the motor's torque for fast walking speeds.

Another aspect of the invention is directed to a method of modifying characteristics of an ankle-foot prosthesis or orthosis apparatus. The method includes the steps of predicting what a walking speed will be during an upcoming step and modifying a characteristic of the apparatus during the upcoming step in situations when the predicted walking speed is slow. The modification of the characteristic results in a reduction in net non-conservative work that is performed during the upcoming step as compared to the net non-conservative work that is performed when the predicted walking speed is fast.

Another aspect of the invention is directed to an apparatus that includes a proximal member and a distal member that is operatively connected with respect to the proximal member by a joint so that an angle between the distal member and the proximal member can vary. A motor is configured to vary the angle between the distal member and the proximal member, and a series elastic element is connected between at least one of (a) the motor and the proximal member and (b) the motor and the distal member. There is a least one first sensor having an output from which a walking speed of an upcoming step can be predicted, and at least one second sensor having an output from which a joint torque can be determined. The apparatus also includes a controller configured to control the motor's torque, based on the output of the at least one first sensor and the at least one second sensor, so that the motor's torque for slow walking speeds is lower than the motor's torque for fast walking speeds.

Another aspect of the invention is directed to an ankle-foot prosthesis or orthosis apparatus that includes a shank member and a foot member that is operatively configured with respect to the shank member so as to supporting walking and permit the foot member to plantarflex and dorsiflex with respect to the shank member. A motor is configured to plantarflex the foot member with respect to the shank member, and a series elastic element is connected between at least one of (a) the motor and the shank member and (b) the motor and the foot member. The apparatus also includes at least one sensor having an output from which a deflection of the series elastic element can be determined, and a controller configured to determine a desired torque based on the output, and to control the motor's torque based on the determined desired torque.

Another aspect of the invention is directed to a method of controlling an ankle-foot prosthesis or orthosis having a foot member and shank member, with a motor configured to plantarflex the foot member with respect to the shank member and a series elastic element in series with the motor. The method includes the steps of sensing a position of the motor, determining a deflection of the series elastic element while the motor is at the position sensed in the sensing step, and controlling the motor's torque based on the motor position sensed in the sensing step and the deflection determined in the determining step.

Another aspect of the invention is directed to an apparatus that includes a proximal member, a distal member that is operatively configured with respect to the proximal member so that an angle between the distal member and the proximal member can vary, and a motor configured to vary the angle between the distal member and the proximal member. A series elastic element is connected between at least one of (a) the motor and the proximal member and (b) the motor and the distal member, and at least one sensor having an output from which a deflection of the series elastic element can be determined. The apparatus also includes a controller configured to determine a desired torque based on the output, and to control the motor's torque based on the determined desired torque.

BRIEF DESCRIPTION OF THE DRAWINGS

FIG. 1 is a schematic illustration of the phases of a user's gait cycle when walking on level ground.

DESCRIPTION OF THE PREFERRED EMBODIMENTS

Figure 2A:
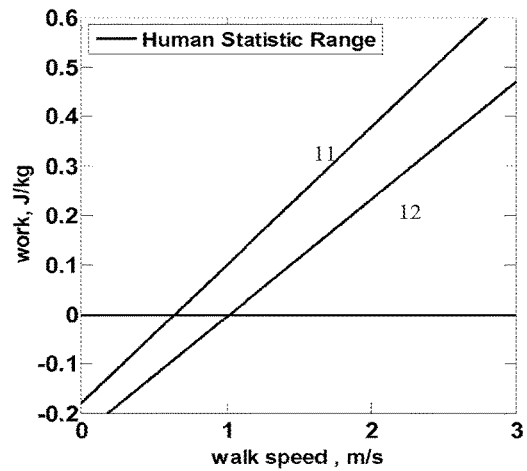
FIG. 2A depicts the statistic range of net non-conservative work vs. walking speed for healthy human ankles.
Figure 2B:
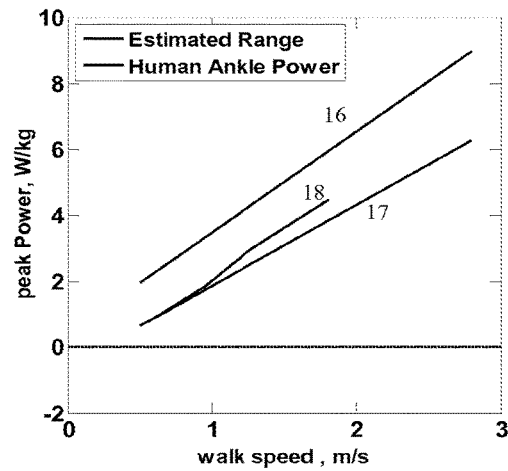
FIG. 2B depicts the statistic range of peak-power vs. walking speed for healthy human ankles.

In healthy humans, the ankle-foot normally creates the positive net-work and peak-power on each stride that the body needs to achieve ordinary walk with metabolic efficiency. The net-work and peak-power in the ankle during the stance of gait is highly related to walking speed. FIGS. 2A and 2B depict this relationship. More specifically, FIG. 2A shows the statistic range (+1 sigma bounds) of net non-conservative work vs. walking speed, which lies between the lines 11, 12. FIG. 2B shows the estimated statistic ranges (+1 sigma bounds) of the peak-power vs. walking speed as lines 16, 17. FIG. 2B also shows the mean value of peak-power vs. walking speed (as measured in a study) as line 18, which lies between lines 16 and 17.

Figure 2C:
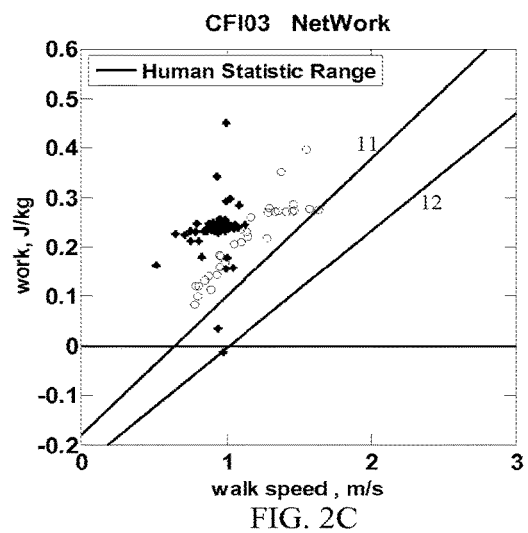
FIG. 2C shows the net non-conservative work vs. walking speed when two different equations are used to control a motor.
Figure 2D:
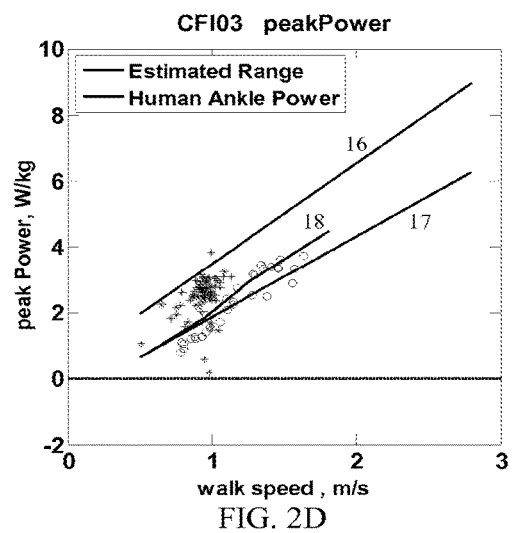
FIG. 2D shows peak-power vs. walking speed when two different equations are used to control a motor.
Figure 10:
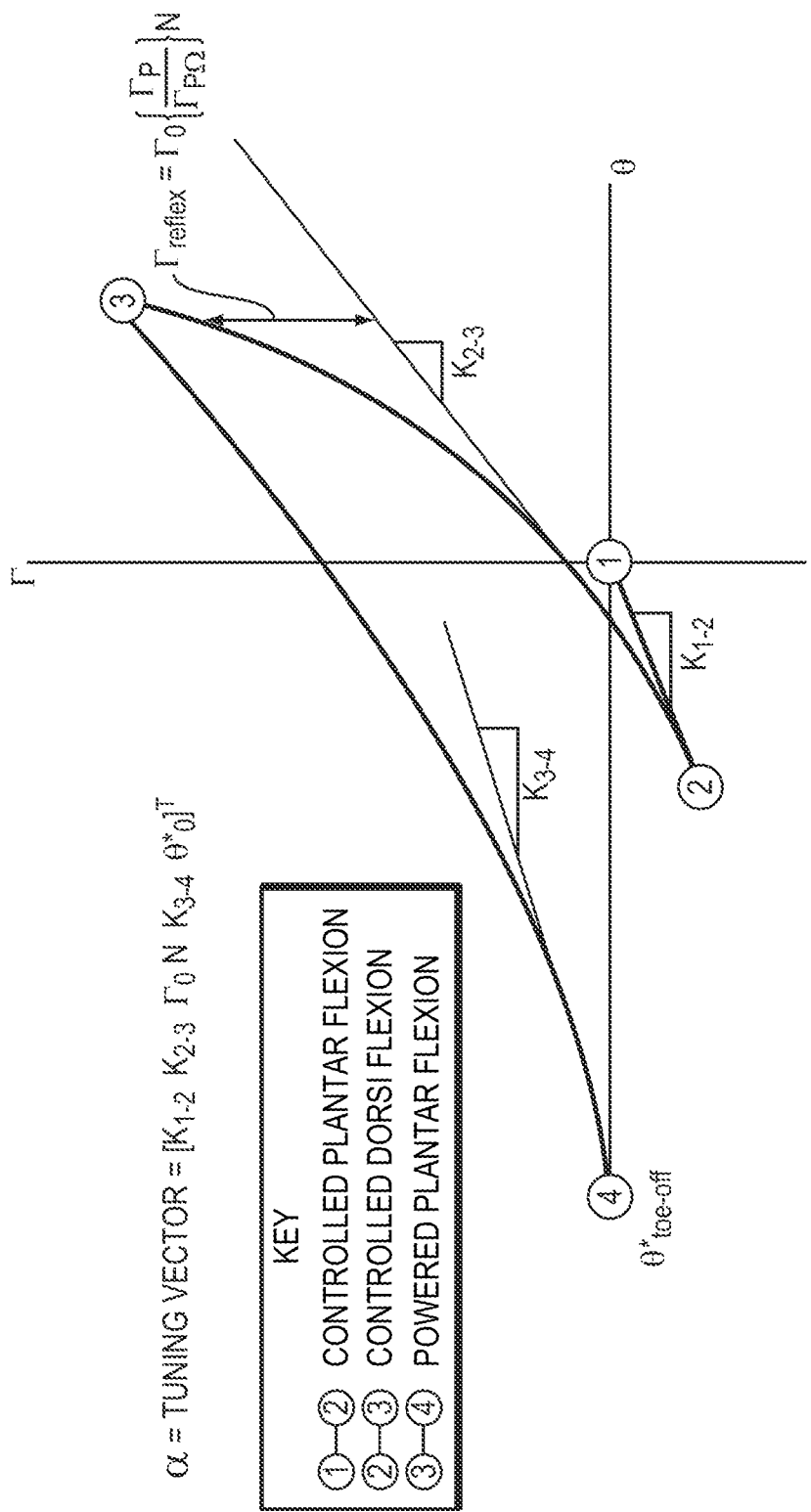
FIG. 10 is a $\Gamma$-$\Theta$ plot for the stance-phase torque-angle response of an intact ankle.

The data points depicted by stars in FIG. 2C shows the net non-conservative work vs. walking speed when Equation 1 above is used to control the motor current. Note that net non-conservative work can be determined by calculating the loop area, over one cycle of ankle-torque vs. ankle angle (e.g., as seen in FIG. 10, starting at point 1, passing through points, 2, 3, and 4 in sequence, and returning to point 1. It can be seen that the net non-conservative work is higher than the statistic range bounded by lines 11,12 for intact ankles, and the deviation from that range is larger at slower walking speeds than it is at faster walking speeds. Similarly, the data points depicted by stars in FIG. 2D show the peak power vs. walking speed when Equation 1 above is used to control the motor current. It can be seen that the peak power is higher than the mean value line 18 for intact ankles. The net work is also higher, and is wasted, causing extra heat and reduction in battery life.

To more closely mimic the human ankle-foot biomechanics for ordinary walk across a wide range of walking speeds, the embodiments disclosed in the '384 application may be modified by using the power control approach described herein so as to deliver net-work and peak-power on each stride that more closely matches the statistic ranges bounded by the lines 11, 12 in FIG. 2A, and the mean line 18 in FIG. 2B. In this approach, a prediction of the walking speed for the upcoming step is made, and that predicted walking speed is used to set the ankle control parameters (including setting of the power control gain) for the upcoming step.

Figure 3A:
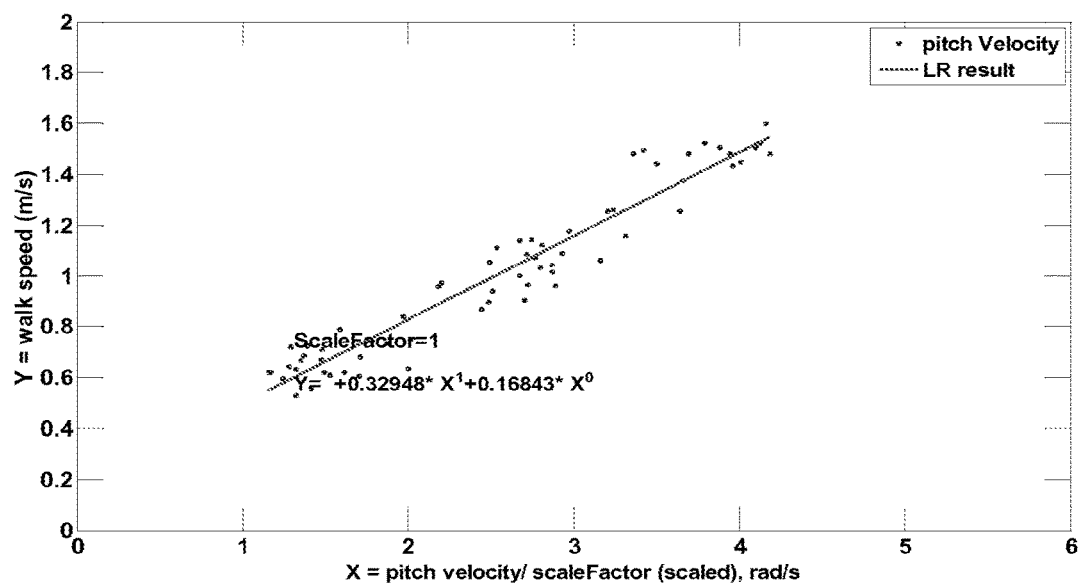
FIG. 3A depicts the relationship between walking speed of the upcoming step and the shank angular rate.

One way to predict the walking speed of the upcoming step is based on the shank (pitch) angular rate $\omega_x$ based on the relationship depicted in FIG. 3A. These two velocities are highly linearly correlated such that the peak angular rate in stance phase serves as an excellent prediction of the walk speed of the up coming step. The correlation between walking speed and the shank angular rate is present at various times during the stance and swing phase, but it is preferable to minimize the latency between the walking speed estimate and when it will be applied. One way to accomplish this is to sample the shank angular rate at the very start of controlled dorsiflexion (i.e., at foot-flat), immediately before the reflex begins. This reduced latency ensures that a reflex is not applied in certain situations, such as when the user is stopping. If, on the other hand, a stale walking-speed prediction were used, (e.g., by estimated walking speed from the shank angular rate at the prior toe-off), the estimate might be invalid (e.g., in situations where the user decides to stop suddenly).

Figure 3B:
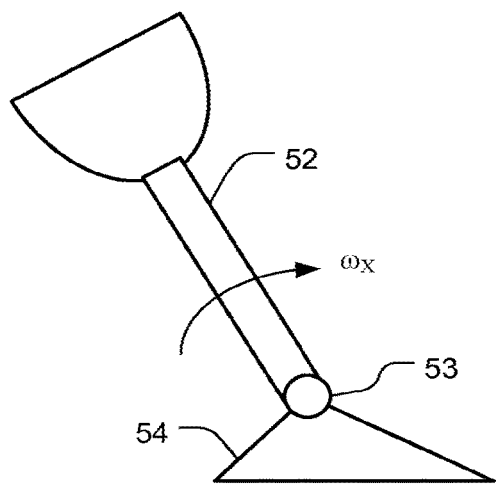
FIG. 3B depicts what shank angular rate is used in FIG. 3A.

The shank angular rate may be measured by any suitable means, such as an inertial measurement unit (IMU) or an angular rate sensor (ARS). The IMU or ARS may be placed onto the top part of the prosthesis or orthosis that is rigidly connected to a socket such that shank angular rate, as depicted in FIG. 3B, can be measured. In alternative embodiments, it could be mounted on the foot structure. An example of a suitable angular rate sensor is the Invensense IDG-300. In one preferred embodiment, the IMU can be made from three orthogonally-aligned angular rate sensors such as the Analog Devices ADXRS610, and three orthogonally-aligned accelerometers such as the Freescale MMA7360L.

An advantage of using the angular rate sensing technique is that it provides an instantaneous measure of angular rate just prior to invoking the reflex control. More specifically, the maximum angular rate in the stance phase can be calculated and employed to adjust the reflex torque response during the controlled dorsiflexion and powered plantar flexion phases of a step. This reflex is largely responsible for generating the net-work and peak-power that meet human ankle-foot needs for ordinary walking.

Figure 4A:
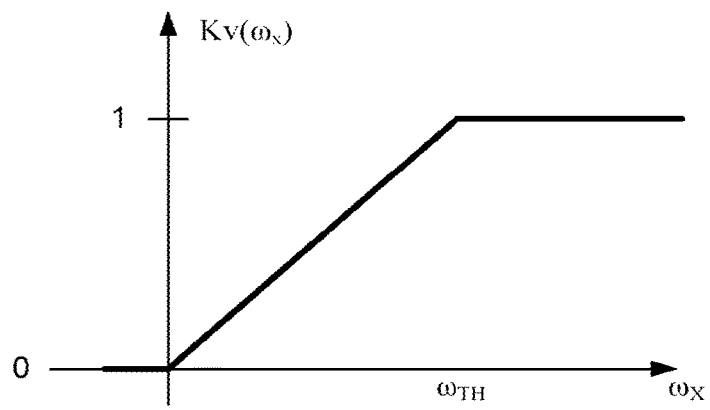
FIG. 4A depicts one suitable gain function for use in controlling the motor.

The reflex torque generation is achieved via non-linear, positive feedback between the series elastic element (SEE) motor torque and ankle torque by controlling the motor using the following equation:

$$\text{Motor Torque} = Kv(\omega_x) \times pff \times (\text{normalized\_Torque})^n \qquad \text{Eq. 2}$$

where $Kv(\omega_x)$ is a power control gain function related to the maximum angular rate, an example of which is depicted in FIG. 4A; pff is the power control gain tuned for high walking speed; normalized_Torque is the ankle torque, $\Gamma_A$, normalized by a torque, $\Gamma_0$, (strongly related to users' weight); and n is the power exponent, typically in the range of between 3 and 5 for level-ground walking. This is similar to Equation 1 above, except that the right side of the equation is multiplied by a gain function $Kv(\omega_x)$ that is selected to reduce the motor torque for lower angular velocities, which correspond to slower walking speeds. Note that the companion equation for converting a desired motor torque to a drive current for the motor remains the same for all embodiments described herein (i.e., Motor Current=Motor Torque/kt, where kt is the motor torque constant).

One suitable gain function $Kv(\omega_x)$ is depicted in FIG. 4A, which starts at 0 when the angular rate is zero, and increases linearly to 1 at an angular rate $\omega_{TH}$ that corresponds to a fast walking speed. Above that threshold angular rate $\omega_{TH}$, the gain function $Kv(\omega_x)$ remains at 1. A suitable setting for the threshold $\omega_{TH}$ is an angular rate that corresponds to a fast walking speed (e.g., an angular rate that corresponds to a walking speed of between 1.5 and 1.75 meters per second). In some embodiments, the threshold point may be settable by a prosthetist, preferably constrained to some legal range (e.g., to an angular rate that corresponds to a walking speed of between 1.25 and 2 meters per second). In other embodiments, provisions for adjusting the $\omega_{TH}$ set point within a legal range may even be made available to the end user.

The result of multiplying the right side of Equation 2 by $Kv(\omega_x)$ is that the motor will be driven by lower currents for slower walk speeds. That will result in less torque at slower walk speeds (as compared to when Equation 1 is used). When this approach is used to control a prosthetic or orthotic ankle, during the flat-foot portion of the gait the torque will initially be zero. The ankle torque $\Gamma_A$ will start to increase at the end of the controlled dorsiflexion phase. In response to the rising $\Gamma_A$, the controller will drive the motor based on Equation 2, which will increase the torque further in a positive feedback reflex response. This positive feedback continues until prior to toe-off as the lower leg begins to lift the foot off the ground. At this point the positive feedback is diminishing, so the torque starts to drops off. The positive feedback is quenched at toe-off because at that point there is nothing to push against, which makes the torque fall off rapidly. In addition, the state machine that controls the application of the reflex also transitions to the swing phase where position control is used. Note that operation of the state machine is described in the '384 application, which is incorporated herein by reference.

The speed based power control method of Equation 2 has been implemented and tested on an iWalk™ Powerfoot™ BiOM™ prosthetic ankle/foot. When Equation 2 was used to control the motor, the net non-conservative work vs. walking speed is depicted by the circle data points in FIG. 2C. A comparison between the circle data points and the star data points (discussed above) in FIG. 2C reveals that the net non-conservative work is closer to the statistic range bounded by lines 11, 12 when Equation 2 is used. Similarly, the circle data points in FIG. 2D show the peak power vs. walking speed when Equation 2 above is used to control the motor current. It can be seen that the peak power when Equation 2 is used is much closer to the mean value line 18 than when Equation 1 is used (indicated by the star data points in FIG. 2D). This experiment result was obtained from a patient with weight of 240 lb and shank length of 53 cm. The walk speed was measured using IMU systems, and ranged from 0.8 m/s to 1.5 m/s. The system provided smooth transitions of power when users randomly changed their walking velocities.

Figure 4B:
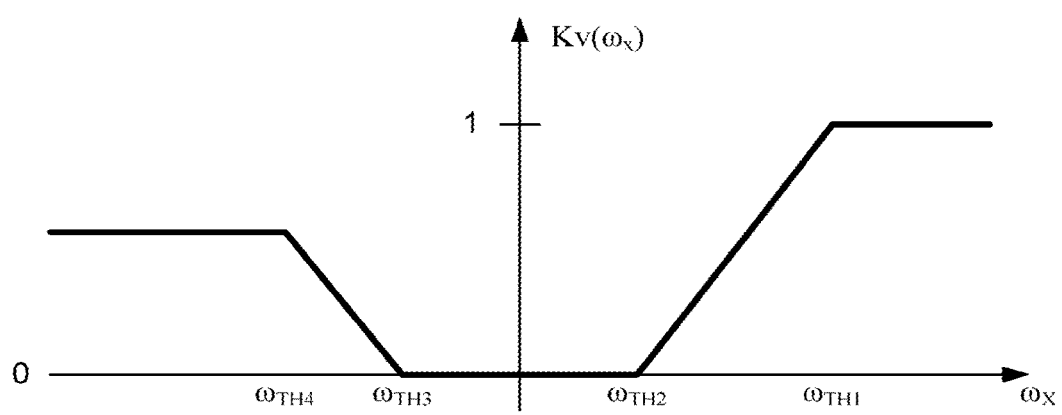
FIG. 4B depicts another suitable gain function.

In alternative embodiments, gain functions with other shapes may be used instead of the ramp depicted in FIG. 4A. Preferably, all such functions start at 0 when $\omega_x=0$, end at 1, and are monotonically increasing. Examples of suitable shapes for the gain function include shapes that resemble (a) the first quadrant of a sine curve; or (b) the third and fourth quadrants of a cosine curve (scaled and offset so as to start at 0 and end at 1). Other transition shapes, including smooth shapes and shapes with abrupt changes, may also be used. For example, the curve depicted in FIG. 4B would operate to keep the power low for low walking speeds (which would be suitable in certain situations like a classroom), and increase it only if the speed goes over a threshold $\omega_{TH2}$. Optionally, the gain function may also be operative for negative velocities to control the reflex response when walking or running backward. For this reason, negative velocities are included in FIG. 4B. If desired, the maximum gain for negative velocities may be lower than 1, so as to provide a smaller power boost when walking backwards In some embodiments, the gain function could also be made to be a function of velocity when side-stepping or hopping sideways.

In some embodiments, a user interface may be provided to give the prosthetist control over the value of n in Equation 2, preferably constrained within some legal range (e.g., between 2 and 7). Set points of between 3 and 5 have been found to be preferable. Since normalized_Torque is $\Gamma_A$ normalized by $\Gamma_0$, when n is high (e.g., around 5), the current will not rise until $\Gamma_A$ gets closer to $\Gamma_0$. This delays (in time) the onset of the positive feedback. Conversely, when n is lower (e.g., around 3), the current will start to increase before $\Gamma_A$ gets too close to $\Gamma_0$. This advances (in time) the onset of the positive feedback. When the system is configured to give the prosthetist control over n, n can be adjusted (e.g., based on verbal feedback from the end user) to maximize the user's comfort. In other embodiments, a user interface may be provided to give the end user control over n (within a legal range).

In alternative embodiments, the reflex torque generation equation may be modified to be as follows:

$$\text{Motor Torque} = Kv(\omega_x) \times pff \times (\text{normalized\_Torque})^{n f(\omega_x)} \qquad \text{Eq. 3}$$

Equation 3 is very similar to Equation 2, except that in Equation 3, the exponent n of the normalized_Torque is multiplied by a function of the angular rate $\omega_x$. The function $f(\omega_x)$ is preferably selected so that the resulting exponent is larger at higher angular velocities than it is at lower angular velocities. This would operate to advance the onset of reflex (in time) when the user is walking faster, with respect to the timing when the user is walking slower.

Note that in the embodiments described above, the system does not explicitly make a prediction of the walking speed for the upcoming step. Instead, the system relies on the angular rate $\omega_x$ of the shank (which, as described above, is correlated to the predicted walking speed). In this case, the angular rate $\omega_x$ of the shank serves as a surrogate for the walking speed. In alternative embodiments, instead of relying on the angular rate $\omega_x$ of the shank, other parameters may be used to predict the walking speed. The ankle power would then be adjusted accordingly based on the predicted walking speed based on these alternative sensors. For example, the angular rate of the leg section above the knee, or the knee linear moving velocity in stance phase may be used to predict the walking speed of the upcoming step. The Cartesian trajectory of the ankle or knee, tracked using an IMU, could also be used to predict the walking speed of the upcoming step.

In other embodiments, the equations may implemented so as to explicitly compute the estimated walking speed as an intermediate result, and then adjust the various parameters based on that intermediate result to control the power and net non-conservative work (e.g., by replacing $Kv(\omega_x)$ with Kv(speed) in Equation 2).

Preferably, the system includes special-event handing to modify the power level when it determines that a special walking environment exists. For example, the power may be increased for upstairs/up-ramp walking, even though the walk speed is low. Or the power may be decreased for down stairs or down ramp walking even though the walk speed is high. Note that the ankle trajectory or knee trajectory (determined, for example, using an IMU) may be used as a discriminator to determine if a special walking environment exists, so that the characteristics of the ankle (including the reflex) can be adjusted for the special walking environment.

The system described above provides users improved net-work and peak-power to achieve normal biomechanics for ordinary walking across a range of walking speeds. The system also uses reduced motor current at low walking speeds, which is the case for the majority of walking in most people's routines. This may help keep the motor temperature low, save energy, and reduce the frequency of recharging batteries and the need to carry spare batteries. Lower currents also reduce the stress and fatigue on the drive transmission, including the series-spring, and can increase the design life of various components in the device.

The embodiments described above rely on the ankle torque $\Gamma_A$ as an input to the equations that ultimately control the motor current during controlled dorsiflexion and powered plantar flexion. This ankly torque $\Gamma_A$ may be determined by a number of approaches. One such approach, which is described in the '384 application, is to actively measure the ankle torque $\Gamma_A$ using, for example, strain gauges arranged in a Wheatstone bridge configuration to measure the torque applied by the socket attachment at the top of the ankle prosthesis.

Figure 5A:
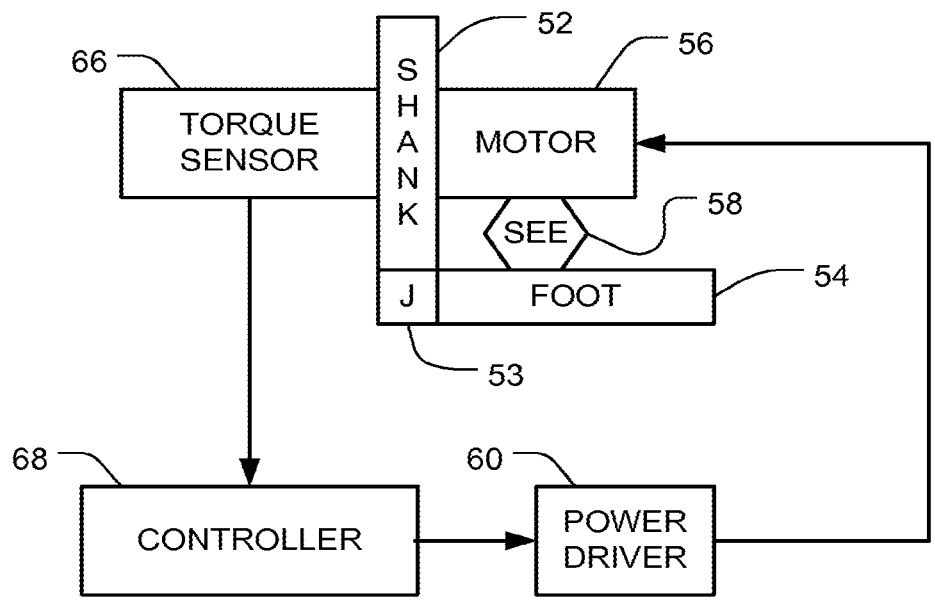
FIG. 5A is a block diagram of an embodiment that relies on torque sensing.

FIG. 5A is a system block diagram for this embodiment. The prosthetic or orthotic ankle/foot includes a shank member 52 and a foot member 54 operatively connected to permit plantarflexion and dorsiflexion, e.g., by a joint 53. A motor 56 is affixed to the shank member 52, and a series elastic element 58 sits between the shank member 52 and the foot member 54, so that it will be in series with the motor, as explained in U.S. Pat. No. 5,650,704, which is incorporated herein by reference. Driving the motor in one direction or the other will plantarflex or dorsiflex the foot member 54 with respect to shank member 52. In alternative embodiments (not shown) the positions of the motor 56 and the series elastic element 58 could be swapped, in which case the motor would be mounted to the foot member 54.

A torque sensor 66 measures the ankle torque $\Gamma_A$ and send an output that represents that torque to the controller 68. The controller 68 is programmed to control the motor 56 by implementing Equation 2. In alternative embodiments, analog circuitry configured to implement Equation 2 may be used in place of the controller 68. The power driver 60 contains the drive circuitry needed to convert the low level signals from the controller 68 into the high power signals needed to drive the motor 56.

Figure 5B:
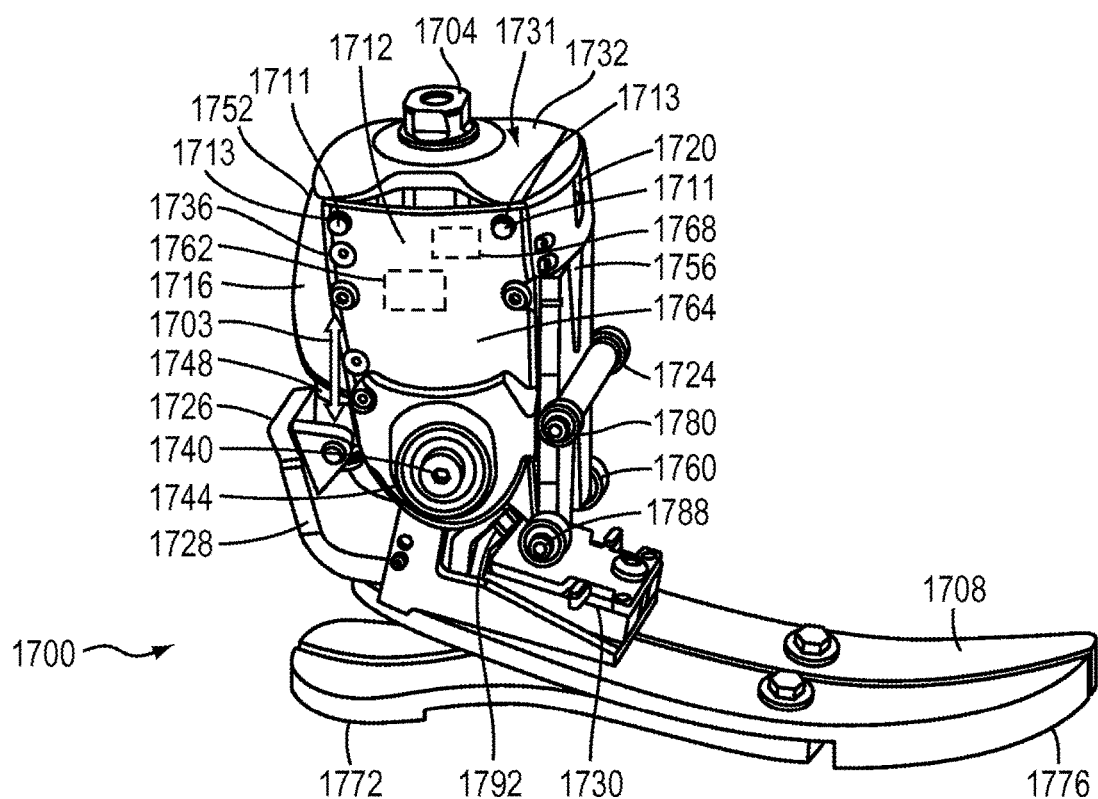
FIG. 5B depicts a mechanical configuration for the FIG. 5A embodiment.

FIG. 5B depicts a practical mechanical configuration for implementing the architecture shown in the FIG. 5A embodiment. In FIG. 5B, the torque sensor 1732 (which corresponds to ref. #66 in FIG. 5A) is positioned at the very top of the shank member 1716 (which corresponds to ref. #52 in FIG. 5A).

Another approach for determining the ankle torque $\Gamma_A$ is to break that torque up into its constituent components, and analyze the torque of each of those components separately. For example, in the design depicted in FIG. 6A-C, there are two components that contribute to the total torque: the torque applied by the series elastic element ($\Gamma_S$) and the torque applied by the bumper ($\Gamma_B$). The bumper is positioned between the shank portion of the ankle and the foot portion, and can also be considered a hardstop when the stiffness is high. In alternative embodiments, a spring may be used instead of a bumper. Note that the $\Gamma_B$ component only comes into play during bumper engagement (i.e., during dorsiflexion, when the shank member presses against a bumper that is affixed to the foot member, or, in alternative embodiments, when the foot member engages a bumper that is affixed to the shank member).

If each of the contributing components is known, the total ankle torque can be determined by vector-adding $\Gamma_S$ and $\Gamma_B$ (i.e., $\Gamma_A = \Gamma_S + \Gamma_B$). In the design depicted in FIG. 6B, both $\Gamma_S$ and $\Gamma_B$ can be determined as a function of displacement as measured by position sensors that are distributed throughout the design, like a motor encoder that detects the position of the motor and an ankle angle encoder that detects the angle of the ankle pivot.

We begin with $\Gamma_S$. In FIG. 6C, the motor 1B-102 drives a ballscrew 1B-106, and a digital encoder 1B-104 mounted on the motor measures the ballscrew extension p. If the foot were to be operated unloaded (e.g., when it is up in the air), for every given value of ballscrew extension p, the ankle joint 1B-108 would move to an angle β(p). The β(p) function can be determined empirically by lifting the device in the air so that it is unloaded, then driving the motor through its entire operating range, and measuring the resulting angle of the ankle joint 1B-108 at each value of p. Alternatively, β(p) could be calculated based on the known geometry of the device. The β(p) function is stored in a memory that is accessible by the controller 78 (shown in FIG. 6A) in any suitable format (e.g., as an equation or a lookup table).

During normal operation, the device will be loaded, and the actual angle θ of the ankle joint 1B-108 can be determined (e.g., by a high-resolution encoder, not shown, mounted on the ankle joint). In addition, the actual ballscrew extension p can be determined based on the output of the digital encoder 1B-104. The controller inputs p from the motor encoder and retrieves the unloaded angular position β(p) from memory. It then inputs the actual angle θ from the ankle joint angle encoder and subtracts β(p) from θ (i.e., the controller computes θ−β(p)). That difference is the angular deflection of the SEE 1B-110. In some embodiments, a "single-turn" motor controller can be used. At power on, its absolute position within one motor turn and the absolute joint position can be used together to determine the absolute displacement of the ballscrew in relation to the end-of-travel in the plantarflexion direction.

Figure 9:
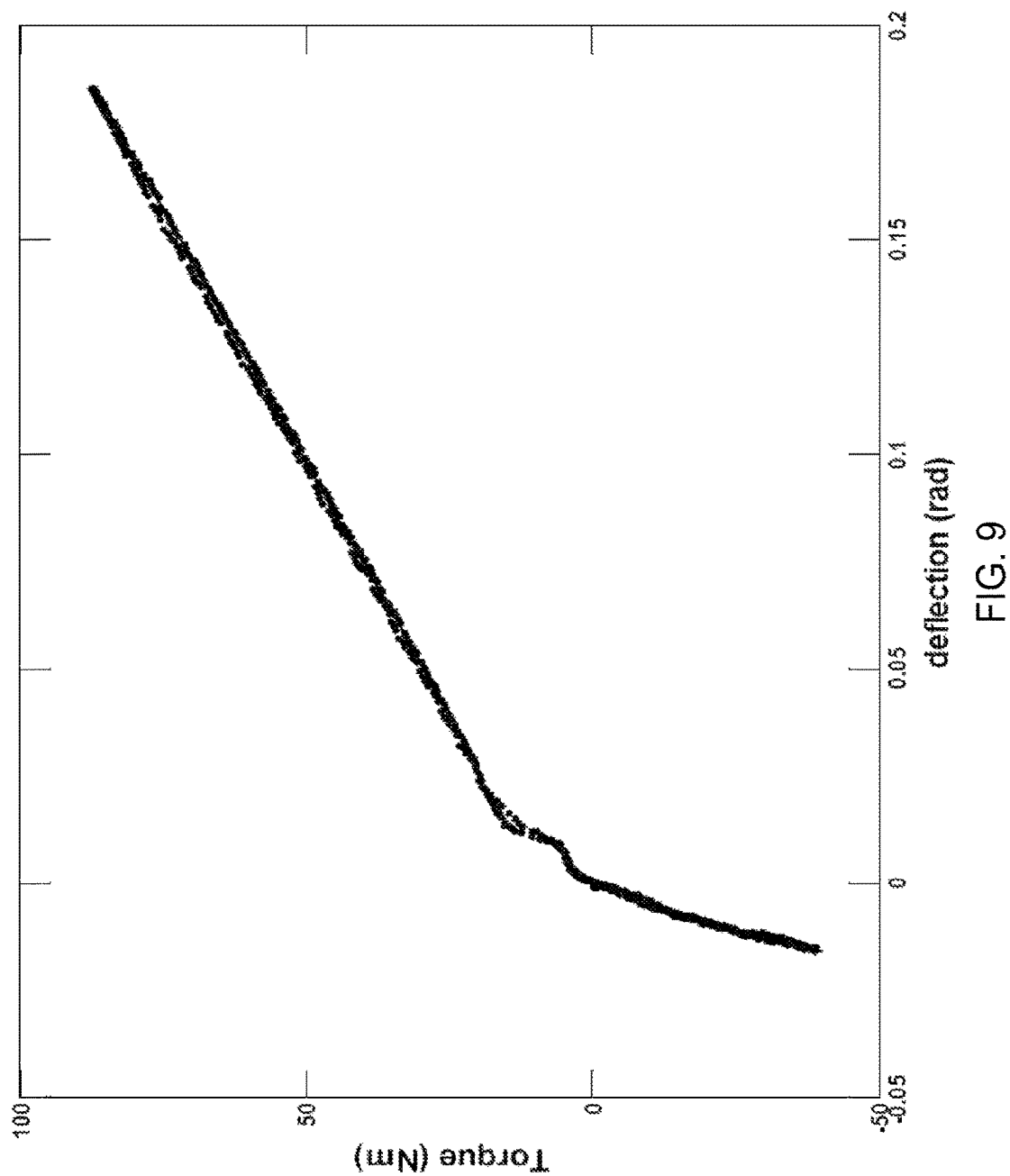
FIG. 9 depicts the torque vs. deflection characteristics for a series elastic element.

After the deflection has been determined, the torque $\Gamma_S$ can be found because torque is a function of the deflection. In a simple model, the torque vs. deflection characteristics can be modeled as a linear function (Hooke's Law), so that $\Gamma_S = k_S \times$ deflection, where $k_S$ is the spring rate for the SEE. FIG. 9 depicts the torque vs. deflection characteristics for the series elastic element 1B-110 (shown in FIG. 6B). From these characteristics, a measured deflection can be used to determine $\Gamma_S$. Note that relying on an equation involving a spring constant $k_S$ is just one of many possible ways to determine the torque from a deflection, and alternative models and approaches for determining the torque vs. deflection characteristics may also be used (e.g., a lookup table, polynomial curve fitting, or non-linear estimation).

We turn next to the $\Gamma_B$ component. During dorsiflexion, the shank member 1B-111 pushes towards the foot member 1B-114, and a bumper 1B-112 that sits between those two members (and could be affixed to either member) is compressed. During testing of the previous generation designs, which used a relatively soft plastic for the bumper 1B-112, the inventors recognized that there is observable compliance in the bumper during engagement, in the range of 0.25° of deflection per 85 Nm peak reference load for a 250 lb amputee. When harder plastics are used (e.g., EPDM, with a 95 A durometer), there is much less deflection (e.g., 0.1° of deflection per 85 Nm peak reference load for a 250 lb amputee), and the force-deflection characteristic of this compliance became more stable and more easily modeled. Note that the metal shells that house the ankle mechanism will also flex measurably, and so can the foot structure and the member that contacts the bumper. When the flexural displacements are measured empirically for a particular design or sample of a design (e.g., using a test fixture), all of those flexures would be automatically accounted for.

Figure 6B:
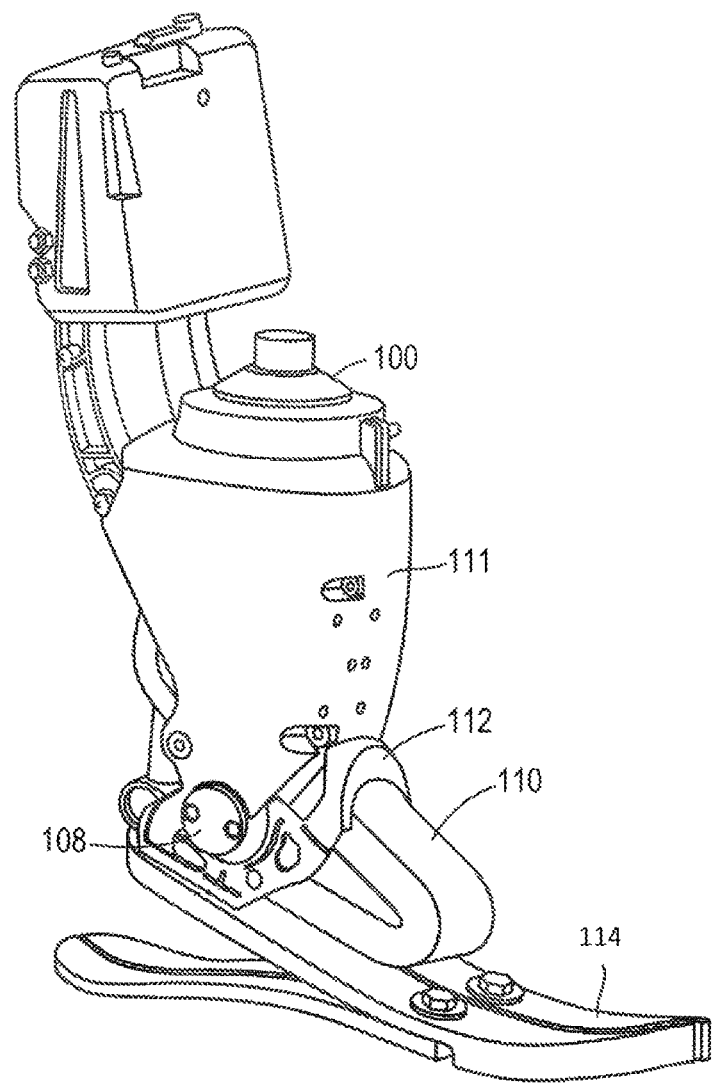
FIG. 6B depicts mechanical configuration for the FIG. 6A embodiment.
Figure 6C:
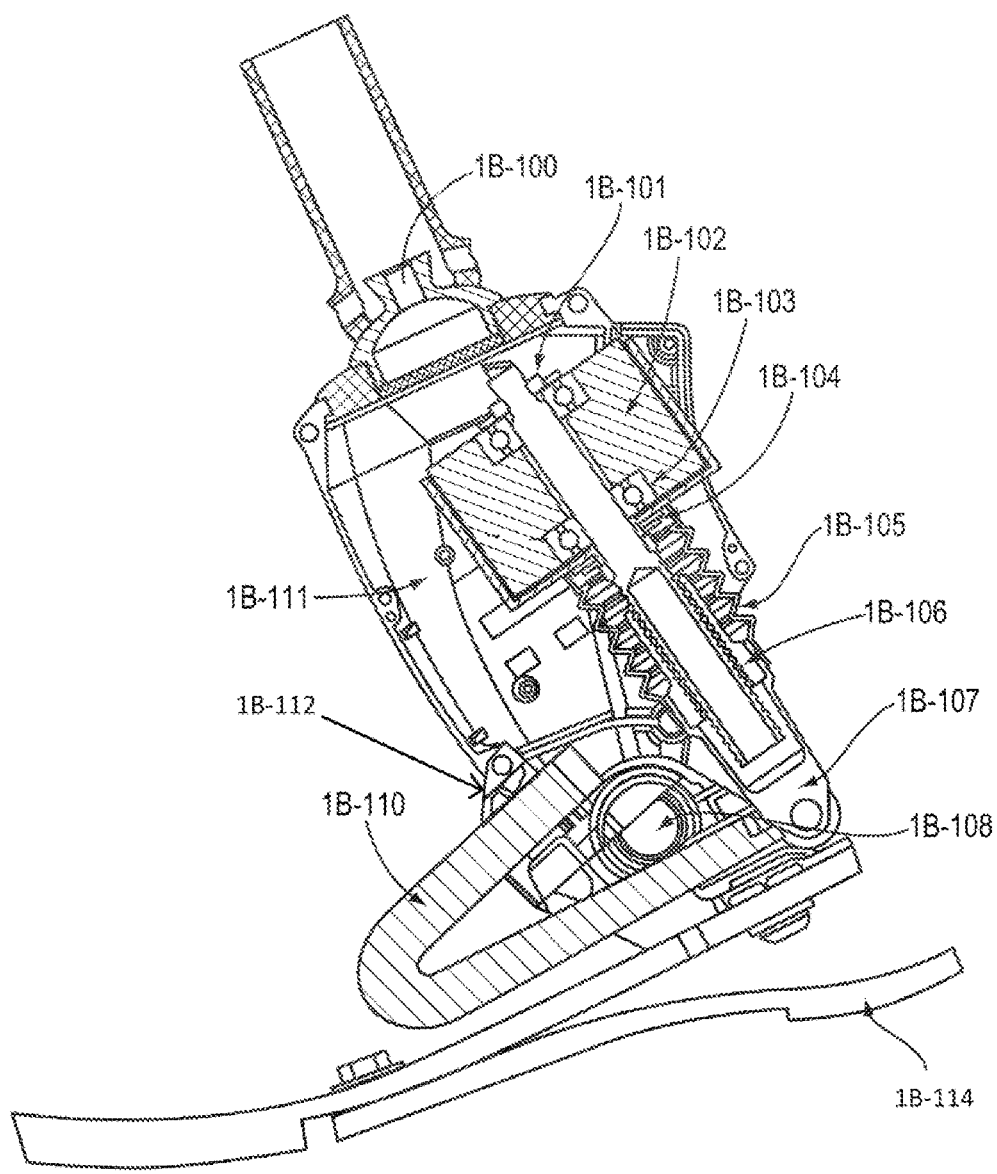
FIG. 6C depicts a section view of the FIG. 6B configuration.
Figure 7:
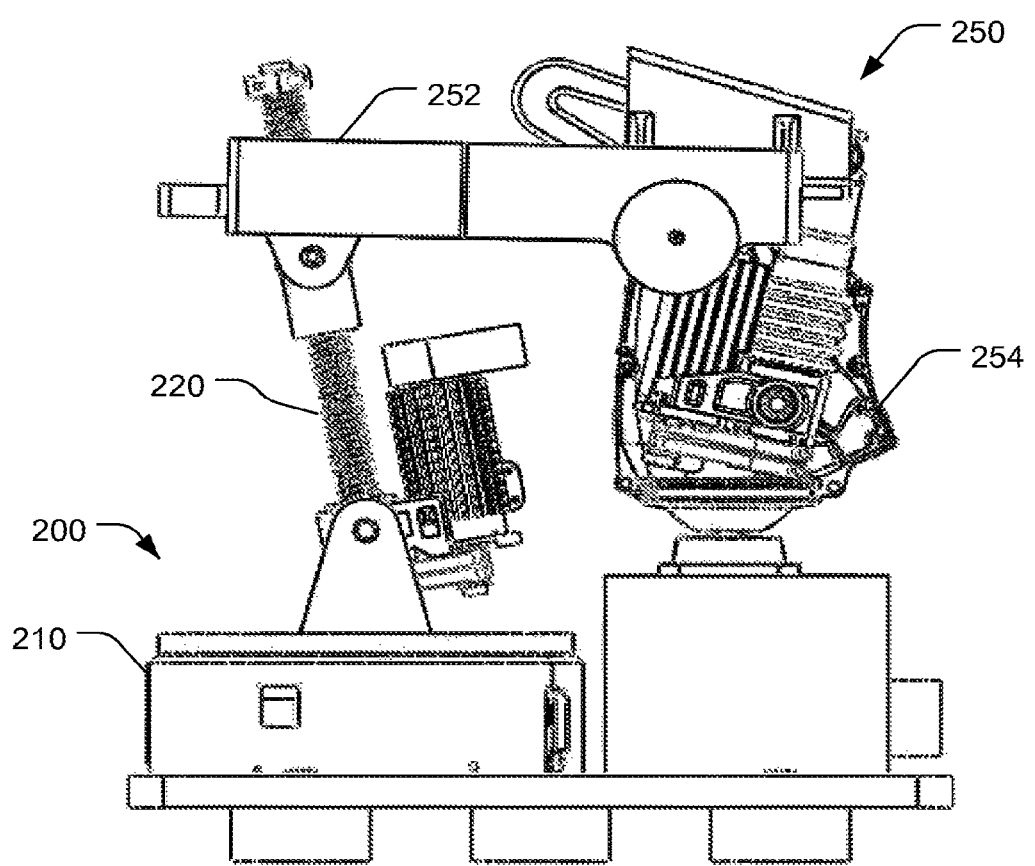
FIG. 7 depicts a test fixture for measuring torque vs. deflection characteristics.

The variation of $\Gamma_B$ with the compression of the bumper can be determined empirically for a given design or a particular instantiation of a design. One way to do this is to bolt a sample ankle/foot 250 into a test fixture 200, like the one shown in FIG. 7. The test fixture 200 preferably uses a six degree-of-freedom force-torque sensor 210 that simultaneously measures force and torque along and about three orthogonal axes (e.g., made by JR3, Inc.), with a backdrive ballscrew actuator 220 installed between the foot portion 252 of the ankle/foot 250 and the JR3 210. In this test fixture 200, the ankle/foot 250 is driven until the foot portion 252 makes initial contact with the bumper (shown in FIG. 6B) on the shank portion 254 of the ankle/foot 250. The angle of initial contact is defined as $\theta_1$. Then, using the backdrive ballscrew actuator 220, the foot portion 252 is further driven to an angle $\theta_C$. The angle $\theta_C$ can be measured by the ankle encoder 1B-108 on the ankle/foot prosthesis (shown in FIG. 6C). As $\theta_C$ increases, the compression of the bumper increases, and the forces as determined by the JR3 210 are stored for every possible angle $\theta_C$.

Figure 8A:
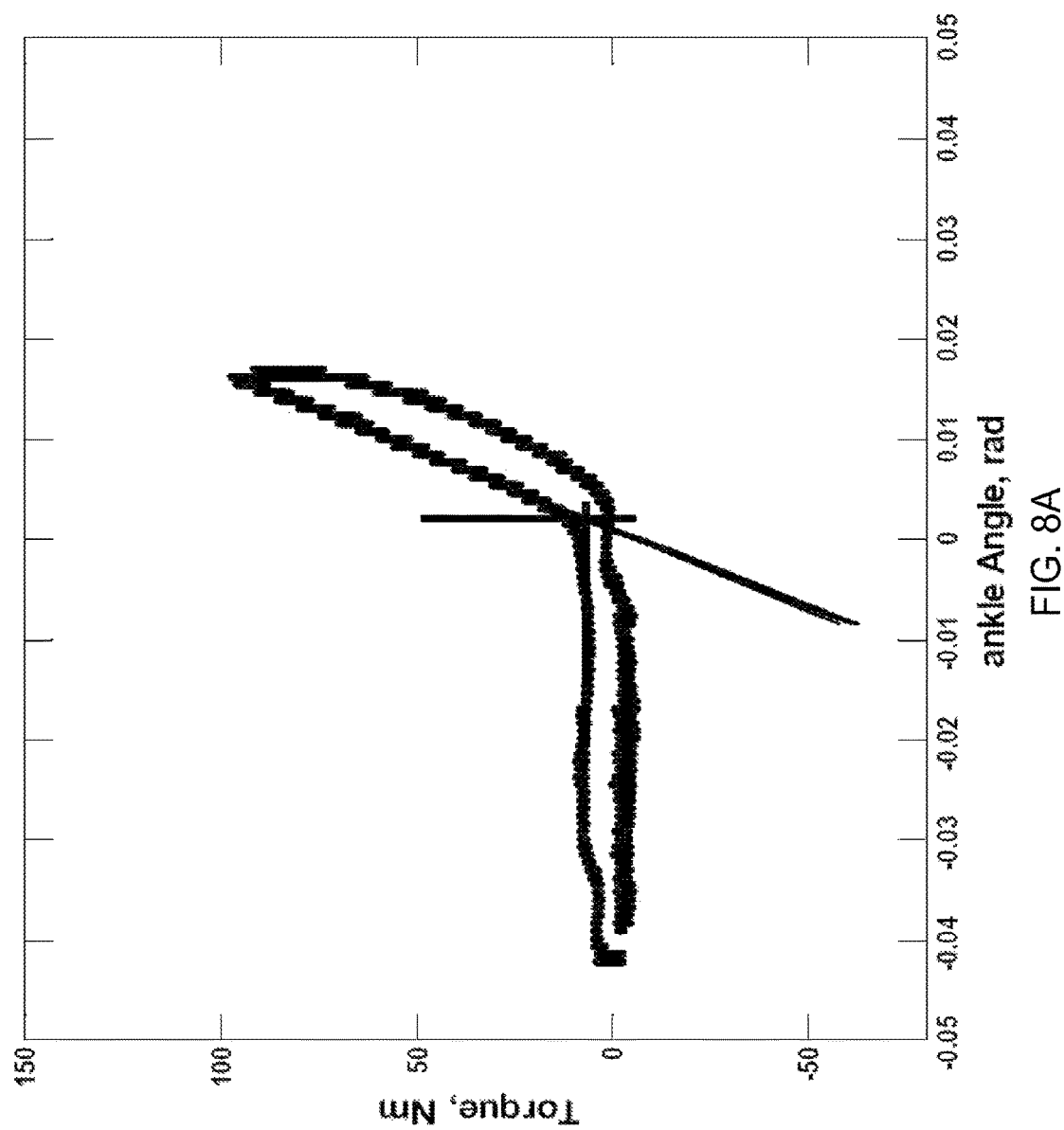
FIG. 8A is a graph from which a spring rate can be determined.

The Z (vertical) and Y (Horizontal) forces measured by the JR3 210 are summed using vector mathematics to determine the force along the backdrive screw axis. The ankle torque is then calculated by multiplying the axial force by the perpendicular moment arm, after subtracting any torque contribution from the SEE. The ankle torque versus ankle angle is plotted for a number of cycles (e.g., 10 cycles) for every possible angle $\theta_C$ and a least squares best fit line is calculated, assuming a linear relationship $\Gamma_B = K_S \times (\theta_C - \theta_I)$, where $K_S$ is the rotational spring rate for the bumper 1B-112. The slope of the resulting best-fit line is the spring rate $K_S$ of the bumper in Nm/rad as shown in FIG. 8A. In alternative embodiments, instead of using this linear relationship to model the bumper, alternative models and approaches for determining the torque vs. deflection characteristics in the design may also be used (e.g., a lookup table, polynomial curve fitting, or non-linear estimation).

Note that when increasing the torque (i.e., when the foot portion is being driven into the bumper and is compressing the bumper), the relationship of the ankle torque to ankle angle deflection is very linear. However when returning back to zero (decreasing torque), the curve is different. This discrepancy is due to the effect of the energy absorbing properties of the bumper. It is preferable to use the slope of the least squares best fit line for the increasing torque portion to determine the spring rate $K_S$ of the bumper.

Figure 8B:
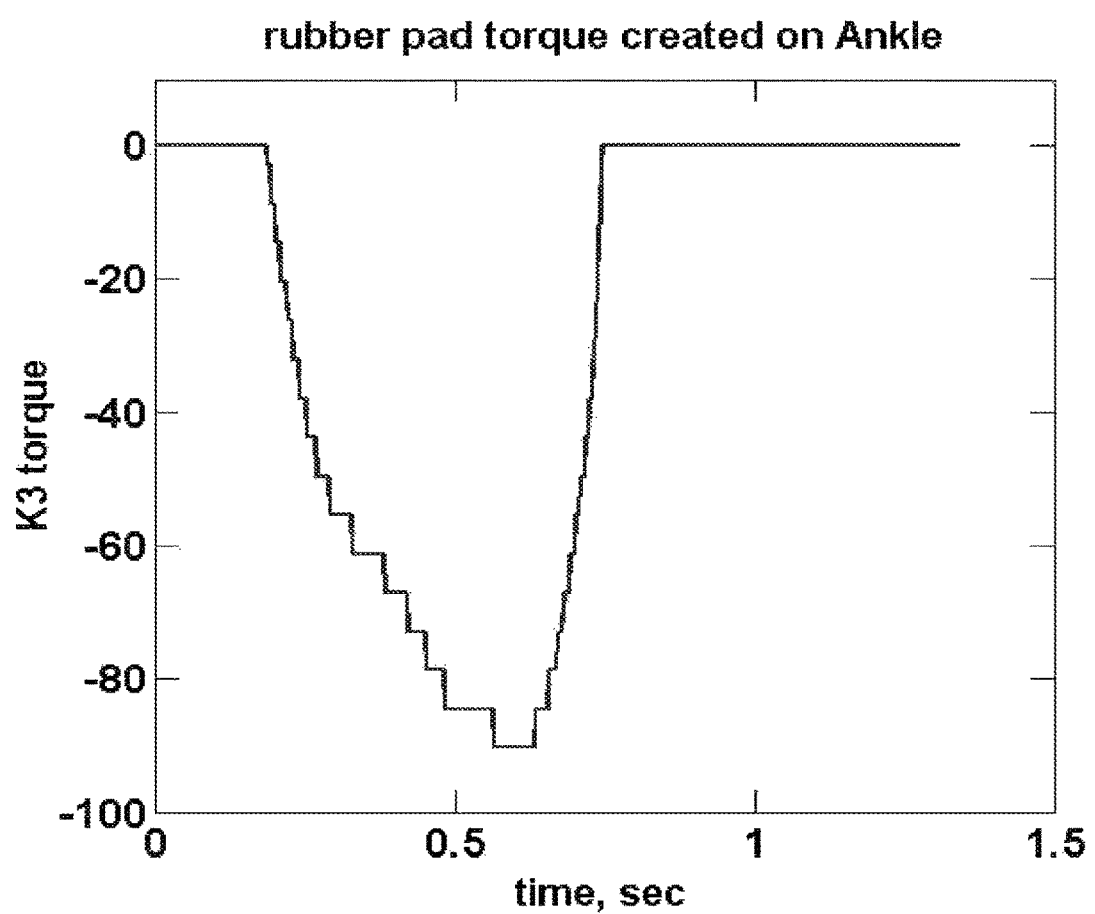
FIG. 8B is a graph depicting changes in a torque component over time.

FIG. 8B depicts the $\Gamma_B$ component of torque that is determined using this approach over time in a situation where the bumper is increasingly compressed for about half a second (until the torque reaches −90), and then released. The quantized nature of the $\Gamma_B$ torque is a function of the encoder resolution. This quantization can be minimized by utilizing higher resolution encoders. In one preferred embodiment, a 13 bit encoder (8196 counts/360 degrees) manufactured by Renishaw Inc (P/N RMB13BC1) is used. The Renishaw encoder employs a custom Hall-effect IC that measures the field angle arising from a single-pole, cylindrical magnet mounted on the foot structure in relation to the orientation of the IC affixed to a printed circuit assembly embedded in the ankle shell. Filtering of the angle measurement, using a FIR Low-Pass filter executing in a dedicated DSP, has been shown to extend the effective resolution to between 15-16 bits.

Once the torque vs. deflection characteristics of a bumper/ankle shell has been modeled (e.g., as explained above), the $\Gamma_B$ contribution at any given instant during operation of the prosthesis can be determined by measuring $\theta_C$ and plugging the result into the equation $\Gamma_B = K_S \times (\theta_C - \theta_I)$, or into an alternative model that models $\Gamma_B$ as a function of $\theta_C$. Thus, from a measured angular deflection $\theta_C$, the second torque component $\Gamma_B$ can be determined. In alternative embodiments, other ankle angle encoding means could be employed to determine how far the bumper has been compressed, including optical, magneto-restrictive and inductive sensors.

At this point, both the $\Gamma_S$ and $\Gamma_B$ components are known. $\Gamma_S$ can now be added to $\Gamma_B$ to arrive at $\Gamma_A$, and the resulting $\Gamma_A$ is used as an input to Equation 2 to control the motor.

Figure 6A:
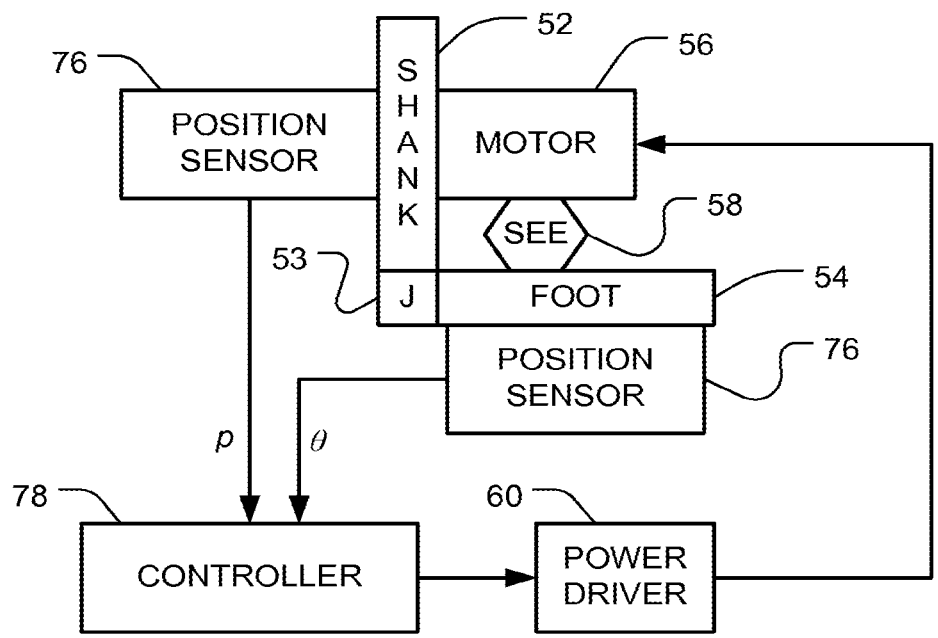
FIG. 6A is a block diagram of an embodiment that relies on deflections and torque vs. deflection characteristics.

FIG. 6A is a system block diagram for implementing this approach by determining $\Gamma_S$ and $\Gamma_B$ separately and then adding those components to arrive at $\Gamma_A$. Elements 52-60 are the same as the correspondingly numbered elements in FIG. 5A. Angular position sensors 76 measure the motor displacement p and the ankle joint displacement θ, and send outputs representing those displacements to the controller 78. The controller 78 is programmed to convert those displacements to torque $\Gamma_S$ as explained above. In addition, the controller 78 is programmed to convert the ankle joint displacement θ to torque $\Gamma_B$ as explained above. The controller 78 then vector-adds $\Gamma_S$ to $\Gamma_B$ to determine $\Gamma_A$. The controller 78 then controls the motor 56 (with the assistance of the power driver 60, as in the FIG. 5A embodiment) by implementing Equation 2.

As mentioned above, n in Equation 2 can be tuned to make the device more comfortable for the user. Other parameters may also be similarly tuned, such as pff and the threshold angular rate $\omega_{TH}$, which affects the $Kv(\omega_x)$ function in Equation 2.

Referring now to FIG. 10, which is a Γ-Θ plot for the stance-phase, body-mass-normalized torque-angle, response of an intact ankle, additional parameters can be found that may be tuned in a prosthesis or orthosis to try to better mimic the intact ankle and thereby improve comfort and performance. Examples include, modulating impedance as the ankle-foot transitions from controlled planter flexion (the slope of $K_{1-2}$), through controlled dorsiflexion (the slope of $K_{2-3}$), to powered plantarflexion (the slope of $K_{3-4}$). The initial values of these three impedances, and the initial value of θ at toe-off ($\theta^*_{TOE-OFF}$) can be derived from the mean Γ-Θ response of intact ankles, and those initial values can then be tuned to suit the activity level, limb length, body-mass distribution and preferences of an individual user.

In the above-described embodiments, a single motor is used to implement both plantarflexion and dorsiflexion. But in alternative embodiments, that motor could be replaced by one motor for implementing plantarflexion, and another component for implementing dorsiflexion. In other alternative embodiments, a plurality of motors may be arranged in parallel to perform both plantarflexion and dorsiflexion. In still other embodiments, the electric motors described above can be replaced with other types of motors (e.g., hydraulic motors), in which case the controller and the power driver will have to be adjusted accordingly.

Note that while the concepts described above are explained in the context of prostheses, they can also be applied in the context of orthoses. In addition, while the embodiments described above all relate to ankles, the above-described concepts can be applied in other prosthetic and orthotic applications, such as hips, torso, and arms, in which case suitable modification should be made that will be appreciated by persons skilled in the relevant arts. For example, in the context of a knee, where the reflex occurs right during toe-off, the walking speed prediction would use "fresh" shank speed measurement just prior to toe-off. In those other contexts, the shank member can be generalized as a proximal member, the foot member can be generalized as a distal member, and dorsiflexion/plantarflexion can be generalized as varying the angle between the distal member and the proximal member. The above-described concepts can also be applied in the context of humanoid robots.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus comprising:
a proximal member;
a distal member that is operatively configured with respect to the proximal member so that an angle between the distal member and the proximal member can vary;
a motor configured to vary the angle between the distal member and the proximal member;
a series elastic element connected between at least one of (a) the motor and the proximal member and (b) the motor and the distal member;
a bumper coupled to at least one of the proximal member and the distal member;
at least one sensor having an output from which a deflection of the series elastic element and a compression of the bumper can be determined, the at least one sensor comprising a sensor that senses a position of the motor and a sensor that senses a sensed angle θ between the distal member and the proximal member; and
a controller configured to determine a torque component $\Gamma_S$ based on the position of the motor, the sensed angle θ, and torque vs. deflection characteristics of the series elastic element, to determine a desired torque based on the output, and to control motor torque based on the determined desired torque.

2. The apparatus of claim 1, wherein the controller is configured to determine the torque component $\Gamma_S$ by subtracting the sensed angle θ from a reference angle β, wherein the controller is configured to determine the reference angle β based on the position of the motor.

3. The apparatus of claim 2, wherein the bumper detected as being compressed when the angle between the distal member and the proximal member distal member exceeds a threshold angle,
wherein the controller is configured to determine a torque component $\Gamma_B$ based on the sensed angle and torque vs. deflection characteristics of the bumper, and
wherein the controller is configured to determine the desired torque based on $\Gamma_S$ and $\Gamma_B$.

4. An ankle-foot prosthesis or orthosis apparatus comprising:
a shank member;
a foot member that is operatively configured with respect to the shank member so as to support walking and permit the foot member to plantarflex and dorsiflex with respect to the shank member;
a motor configured to plantarflex the foot member with respect to the shank member;
a series elastic element connected between at least one of (a) the motor and the shank member and (b) the motor and the foot member,
a bumper coupled to at least one of the shank member and the foot member;
at least one sensor having an output from which a deflection of the series elastic element and a compression of the bumper can be determined, the at least one sensor comprising a sensor that senses a position of the motor and a sensor that senses a sensed angle θ of the foot member with respect to the shank member, and
a controller configured to determine a torque component $\Gamma_S$ based on the position of the motor, the sensed angle θ, and torque vs. deflection characteristics of the series elastic element, to determine a desired torque based on the output, and to control motor torque based on the determined desired torque.

5. The apparatus of claim 4, wherein the motor is also configured to dorsiflex the foot member with respect to the shank member.

6. The apparatus of claim 4, wherein controller is configured to determine the torque component $\Gamma_S$ by subtracting the sensed angle θ from a reference angle β, wherein the controller is configured to determine the reference angle β based on the position of the motor.

7. The apparatus of claim 6, wherein the bumper is detected as compressed when the foot member is sufficiently dorsiflexed with respect to the shank member,
wherein the controller is configured to determine a torque component $\Gamma_B$ based on the sensed angle and torque vs. deflection characteristics of the bumper, and
wherein the controller is configured to determine the desired torque based on $\Gamma_S$ and $\Gamma_B$.

* * * * *